United States Patent
Zacharias

(10) Patent No.: US 8,617,106 B2
(45) Date of Patent: Dec. 31, 2013

(54) POST-OCCLUSION CHAMBER COLLAPSE CANCELING SYSTEM FOR A SURGICAL APPARATUS AND METHOD OF USE

(75) Inventor: Jaime Zacharias, Santiago (CL)

(73) Assignee: Alcon Research, Ltd., Fort Worth, TX (US)

( * ) Notice: Subject to any disclaimer, the term of this patent is extended or adjusted under 35 U.S.C. 154(b) by 973 days.

(21) Appl. No.: 12/664,409

(22) PCT Filed: Jun. 19, 2008

(86) PCT No.: PCT/US2008/067463
§ 371 (c)(1),
(2), (4) Date: Dec. 14, 2009

(87) PCT Pub. No.: WO2008/157674
PCT Pub. Date: Dec. 24, 2008

(65) Prior Publication Data
US 2010/0185150 A1    Jul. 22, 2010

Related U.S. Application Data

(63) Continuation-in-part of application No. 11/766,770, filed on Jun. 21, 2007, now abandoned, and a continuation-in-part of application No. 11/765,223, filed on Jun. 19, 2007.

(60) Provisional application No. 61/050,373, filed on May 5, 2008, provisional application No. 60/971,708, filed on Sep. 12, 2007.

(51) Int. Cl.
*A61M 1/00* (2006.01)

(52) U.S. Cl.
USPC .......................................................... 604/119

(58) Field of Classification Search
USPC .......................................................... 604/119
See application file for complete search history.

(56) References Cited

U.S. PATENT DOCUMENTS

| | | | | |
|---|---|---|---|---|
| 5,569,188 | A * | 10/1996 | Mackool | 604/67 |
| 5,720,742 | A * | 2/1998 | Zacharias | 606/1 |
| 5,810,765 | A * | 9/1998 | Oda | 604/31 |
| 6,425,883 | B1 * | 7/2002 | Urich et al. | 604/119 |
| 6,599,271 | B1 * | 7/2003 | Easley | 604/119 |
| 6,939,317 | B2 * | 9/2005 | Zacharias | 604/22 |
| 2005/0054971 | A1 * | 3/2005 | Steen et al. | 604/22 |
| 2008/0294095 | A1 * | 11/2008 | Zacharias | 604/65 |
| 2008/0319374 | A1 * | 12/2008 | Zacharias | 604/22 |
| 2008/0319451 | A1 * | 12/2008 | Zacharias | 606/107 |
| 2010/0185150 | A1 * | 7/2010 | Zacharias | 604/119 |
| 2012/0022548 | A1 * | 1/2012 | Zacharias | 606/107 |

FOREIGN PATENT DOCUMENTS

EP    1010437 A1 *    6/2000    ............. A61M 1/00

* cited by examiner

*Primary Examiner* — Nicholas Lucchesi
*Assistant Examiner* — Diva K Chander
(74) *Attorney, Agent, or Firm* — Kenneth D. Bassinger

(57) ABSTRACT

A post-occlusion chamber collapse canceling system for a surgical apparatus that detects the breaking of occlusions by tissue fragments in the distal end of the aspiration path and produces a response comprising a transitory blockage of the distal end the aspiration path to terminate the chamber collapse and a simultaneous transitory venting of the aspiration line to relieve the vacuum, in a way that post-occlusion chamber collapses are cancelled.

115 Claims, 24 Drawing Sheets

POST-OCCLUSION CHAMBER COLLAPSE CANCELING SYSTEM FOR A SURGICAL APPARATUS AND METHOD OF USE

CROSS-REFERENCE TO RELATED APPLICATIONS

This application is a continuation-in-part of U.S. application Ser. No. 11/765,223 filed 19 Jun. 2007. This application is also a continuation-in-part of U.S. application Ser. No. 11/766,770 filed 21 Jun. 2007, now abandoned. This application claims benefit of U.S. application Ser. No. 60/971,708 filed 12 Sep. 2007. This application also claims benefit of U.S. application Ser. No. 61/050,373 filed 5 May 2008. This application is a national stage under 35 USC Section 371 of PCT application PCT/US2008/067463 filed 19 May 2008.

BACKGROUND OF THE INVENTION

This invention generally relates to the field of surgery inside a collapsible body chamber and more particularly to a surgical apparatus for removing the lens from an eye.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

Optical aberrations such as myopia, hyperopia, astigmatism and presbiopia can also be corrected by the removal of the natural lens of the eye and the implantation of a suitable IOL in a procedure known as refractive lens exchange identical to the cataract surgery procedure, except for the fact that the lens material is usually easier to remove. The best current standard of care procedure to remove cataractous lenses or perform a refractive lens exchange is a surgical technique called phacoemulsification. During this procedure, a hollow phacoemulsification probe is inserted into the eye through a small incision. The tip of the probe is placed in contact with the lens material and the tip is vibrated ultrasonically. The vibrating probe tip liquefies or emulsifies the lens material so that the lens content may be aspirated out of the eye. The lens content, once removed, is replaced by an artificial lens preferably placed inside the lens capsule bag.

A typical phacoemulsification surgical device suitable for ophthalmic procedures consists of an ultrasonically-driven hand piece, an attached hollow lensectomy probe, a surrounding coaxial irrigating sleeve and a control console. The hand piece assembly is attached to the control console by electric cables and by flexible tubing for irrigation and aspiration.

Through the electric cables, the control console provides power to the actuator in the hand piece that is transmitted to the attached lensectomy probe. The flexible tubing supplies irrigation fluid to and draws aspiration fluid from the eye through the hand piece assembly. Alternative methods for lens fragmentation currently available employ sonic wave, water jet and laser powered lens-disrupting hand pieces. The irrigation and aspiration systems of these alternative lens-removing methods typically operate similarly to standard ultrasonic phacoemulsification.

The operative part of ultrasonic hand pieces is a centrally located, hollow resonating bar or horn directly attached to a set of piezoelectric crystals. The crystals supply the required ultrasonic vibration needed to drive both the horn and the attached probe during phacoemulsification and are controlled by the console. The crystal/horn assembly is suspended within the hollow body or shell of the hand piece by flexible mountings. The hand piece body terminates in a reduced-diameter portion or nosecone at the body's distal end. The nosecone is externally threaded to accept the irrigation sleeve. Likewise, the horn bore is internally threaded at its distal end to receive the external threads of the probe. The irrigation sleeve also has an internally threaded bore that is screwed onto the external threads of the nosecone. The hollow probe is adjusted so that the probe tip projects only a predetermined amount past the open end of the irrigating sleeve. Ultrasonic hand pieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996.

In use, the distal end of the lensectomy probe and irrigating sleeve are inserted into a small incision of predetermined width in the cornea, sclera, or other location. The probe tip is ultrasonically vibrated within the irrigating sleeve by the crystal-driven ultrasonic horn, thereby emulsifying the selected tissue in situ. The axis of vibration of the probe tip can be longitudinal, torsional or a combination. One of the advantages of the torsional system is reduced heat generation at wound level with reduced risk of incision thermal injury. The hollow bore of the probe communicates with the bore in the horn which in turn communicates to an aspirate-out port in the hand piece. A reduced pressure or vacuum source in the console draws or aspirates the emulsified tissue from the eye through the probe and horn bores and the flexible aspiration line and into a collection device.

The aspiration of emulsified tissue is aided by a flushing solution or irrigant that enters into the surgical site through the small annular gap between the inside surface of the irrigating sleeve and the outer surface of the probe. The flushing solution is typically a saline solution and enters the surgical site with a positive pressure created gravitationally or by forced infusion means, such as an adjustable pressurized gas source. Typical irrigation pressures are set between 40 and 130 cm H2O. The preferred surgical technique is to make the incision into the anterior chamber of the eye as small as possible in order to reduce the risk of induced astigmatism. To date these small incisions have had typical widths between 3.5 and 1.8 mm and result in very tight wounds that squeeze the coaxial irrigating sleeve tightly against the lensectomy probe. Friction between the coaxial irrigating sleeve and a vibrating probe generates heat, and probe overheating causing a burn to the tissue is avoided by the cooling effect of the aspirated fluid flowing inside the probe. Occasionally the probe tip becomes occluded with tissue, reducing circulation of the cooling aspirate and allowing the probe to build up heat with the risk of thermally damaging the incision.

An alternative technique called Micro Incision Cataract Surgery (MICS) has become popular as it allows further reductions of the incision dimensions. The main difference with this technique is that the irrigant is no longer delivered into the eye through a coaxial irrigating sleeve located surrounding the lens-disrupting hollow probe. With MICS a second irrigating instrument delivers the irrigant solution into the eye through a second small incision. The bare phacoemulsification probe is introduced without any surrounding sleeve through a tight, low leakage, micro-incision having a width in the range of 0.8 to 1.5 mm. The separate irrigating instrument is introduced through another incision having similar characteristics and dimensions. In this way, the MICS technique delivers the irrigant through a hollow instrument inserted into the eye through a second micro-incision. Aspiration of lens fragments and irrigant solution takes place through the aspiration channel of the hollow vibratory probe. The increasingly-small incisions currently used in the micro coaxial phacoemulsification technique as well as in the MICS technique limit the flow of irrigant into the eye determining the use of low aspirate flow rates to avoid a negative fluidic balance that can collapse the eye during surgery.

When fragments of cataractous tissue occlude the tip of the lensectomy probe, the aspiration pump remains operating and builds a vacuum in the aspiration line. This occlusion typically clears by the action of the built up vacuum aided by vibration of the lensectomy probe. An unwanted phenomenon known as post-occlusion surge can occur when the occlusion clears. This phenomenon results in a transient collapse of the anterior chamber of the eye typically lasting fractions of a second. Post-occlusion surge creates unstable surgical conditions such as anterior chamber shallowing, pupil contraction and corneal instability, all events which can lead to serious complications such as posterior capsule rupture, vitreous loss and lens luxation.

The events which lead to chamber instability are as follows: When the tip of the lensectomy probe becomes occluded by lens fragments, the vacuum that builds up inside the aspiration line contracts the walls of the elastic aspiration tubing. Also, the built up vacuum expands eventual bubbles circulating in the aspirate fluid. These two phenomena add up a volume void. Once the occlusion becomes cleared, the gradient between the positive pressure inside the eye chamber and the negative pressure inside the aspiration line determines a fast inrush of liquid circulating from within the eye chamber into the aspiration line through the now-cleared aspiration probe. This inrush ends after the contracted tubing walls re-expand and the expanded bubbles collapse due to the dropping vacuum. This inrush of liquid may exceed the rate of infusion of irrigant into the eye leading to a transient chamber collapse. As a mode of example, an occlusion break occurring at a vacuum level of 500 mmHg can produce a transient inrush of fluid at a flow rate above 80 ml/min during a fraction of a second. A transient chamber collapse will occur until the irrigation solution refills the eye chamber and dynamic fluidic equilibrium is restored.

Several strategies have been implemented to attempt diminish the chamber collapse that results from the post-occlusion surge phenomenon. To mention some: a) reduction of the maximum allowed vacuum level in the aspiration line, b) increase in the pressure of the irrigant solution, c) prevention of total occlusion by the incorporation of a small bypass port at the sidewall of the lensectomy probe, d) use of aspiration line tubing made from flexible but non-contracting polymers, e) use of high bore tubing in the irrigation line, f) splitting of the irrigation tubing to infuse the irrigant through two incisions, g) use of a particle retainer filter flowed by a narrow fluid passage in the aspiration line (Cruise Control System, Staar, USA), and h) predicting that an occlusion break will occur after a preset interval of occlusion (vacuum rise) and reversing operation of the aspiration pump to set a lower vacuum level before the occlusion actually breaks (CASE enabled, WhiteStar Signature System, AMO, USA). The method of increasing the pressure of irrigant solution delivered by an irrigation probe may indeed help to attenuate the magnitude of post-occlusion-break chamber collapses. However there is concern about using techniques that increase the irrigant pressure to reduce the post-occlusion surge phenomenon because of the risks of chamber instability, pupillary dilatation and contraction, ocular pain, hydration of the vitreous, optic nerve damage, herniated iris and others. Active infusion methods which pressurize the irrigant have been proposed but have the added risk of creating an overpressure inside the eye leading to serious complications.

Some U.S. pre-grant publications which help to define the general state of the art but do not anticipate or suggest the invention to be disclosed here include the following:

U.S. 2006-0078448 by Holden appears to disclose a system where sensing and venting are both performed at console level. Sensing performed near the handpiece, as will be seen herein, dramatically improves performance because of earlier detection of the occlusion break.

U.S. 2006-0173403 by Injev appears to disclose a proportional flow control system located inside a handpiece.

U.S. 2002-0151835 by Ross appears to disclose a pressure pulse on top of a vacuum inside an aspiration line.

U. S. 2006-0224163 by Sutton appears to disclose a surge cancelling method that partially blocks the aspiration line when an occlusion brake event is detected. This approach is not very effective because of the long period of OFF time required to compensate the void in the aspiration path using fluid from the eye flowing through the restricted aspiration channel.

Although many of the aforementioned techniques may help to reduce the problems associated with the post-occlusion surge phenomenon, the increasingly popular tendency to reduce the size of the incisions makes all these measures less effective. In fact post-occlusion surge is still a limiting factor to perform a more efficient lensectomy procedure, for example using higher vacuum levels what would allow removal of the lens using lower amounts of lens-disrupting energy such as ultrasound, in less time, with lower amounts of irrigant solution.

From a medical standpoint, it would be ideal to perform a lensectomy procedure using the lowest amounts of irrigant solution and the lowest amount of lens-disrupting energy. Both irrigant solution circulation and lens-disrupting energy are known to produce surgically induced trauma, such as endothelial cell loss. Therefore, a need continues to exist for an effective post-occlusion chamber collapse canceling system for a lens-removing surgical apparatus, especially to perform micro-incision cataract surgery.

SUMMARY OF THE INVENTION

The present invention improves upon the prior art by providing a post-occlusion chamber collapse canceling system for a surgical apparatus including a control system which prevents the anterior chamber instability associated with the phenomenon of post-occlusion surge. This capability can be achieved by a) detecting the occlusion-break events and then b) activating a transitory actuator-mediated occlusion in the aspiration line, preferably in proximity to the hand piece, and c) activating a transitory actuator-mediated vacuum-relieving action. The vacuum relieving action can be in the form of a venting operation, reverse operation of the aspiration pump or other means for vacuum cancellation in the aspiration line. The incorporation of this control system in a surgical apparatus virtually eliminates the instability of the anterior chamber that results from post-occlusion surges.

One can also prevent post-occlusion surge using an embodiment in which an occluded (blocked) aspiration line is enforced as the default state. Then, under control of the operator, the aspiration line is opened for brief intervals of time at a controlled repetition rate. Such control by the operator prevents the vacuum surge and consequent danger of body chamber collapse This system allows an operator to safely perform lens-exchange procedures through very small incisions using low aspiration flow rates, high vacuum and low irrigant pressure, all factors that reduce surgical trauma. During the periods in which the actuator-mediated aspiration line blockage is active, lens-disrupting energy delivered to the lensectomy probe can be adjusted to prevent thermal injuries related to blocked outflow and poor probe cooling. Micro-coaxial phacoemulsification probes, bimanual micro-incision lensectomy probes, laser phacolysis probes, water jet based liquefracture probes, vitrectomy probes and other kinds of irrigation/aspiration probes used during eye surgery may all benefit from this invention.

Accordingly, one objective of the present invention is to provide a post-occlusion chamber collapse-canceling system for a surgical apparatus to maintain a stable anterior chamber after occlusion-break events even when using high vacuum levels and small incisions.

It is another objective of the present invention to provide a post-occlusion chamber collapse canceling system for a surgical apparatus that allows operation with reduced tissue-disruptive energy such as ultrasound, liquefracture energy and laser energy.

It is another objective of the present invention to provide a post-occlusion chamber collapse canceling system for a surgical apparatus to perform cataract surgery using reduced amounts of irrigant solution.

It is another objective of the present invention to provide a post-occlusion chamber collapse canceling system for a surgical apparatus that allows performing cataract surgery using low infusion pressure with improved eye chamber stability.

It is still another objective of the present invention to provide a post-occlusion chamber collapse canceling system for a surgical apparatus that allows performing cataract surgery more efficiently reducing the operative time.

To achieve these and other objects, the invention disclosed, in a preferred embodiment, is a surgical system and related method for preventing collapse of a body chamber being operated upon, due to a vacuum surge following a clearing of an occlusion in an aspiration path of the surgical system, comprising: an occlusion-break sensor for sensing the clearing of the occlusion; a normally-open occlusion valve, temporarily closing in response to the occlusion-break sensor sensing the clearing of the occlusion, thereby occluding fluid flow through the aspiration path and controllably stabilizing the occlusion break, thereby preventing the vacuum surge and consequent body chamber collapse; and a normally-closed venting valve temporarily opening in response to the occlusion-break sensor sensing the clearing of the occlusion, to reduce the vacuum thereby preventing the vacuum surge and consequent body chamber collapse. In an alternative embodiment, the normally-open occlusion valve may be omitted.

Yet another alternative embodiment, the invention disclosed is a similar surgical system comprising a normally-closed occlusion valve, temporarily opening for a defined interval before returning to a closed stated, and repeating the temporarily opening and closing at a controlled repetition rate, in response to control by an operator of the system, wherein, by opening the aspiration path in response to the control by the operator, flow through the aspiration path is controlled by the operator thereby preventing the vacuum surge and consequent body chamber collapse.

These and other advantages and objectives of the present invention will become apparent from the detailed description and claims that follow.

BRIEF DESCRIPTION OF THE DRAWINGS

The features of the invention believed to be novel are set forth in the appended claims. The invention, however, together with further objects and advantages thereof, may best be understood by reference to the following description taken in conjunction with the accompanying drawing(s) summarized below.

FIGURE LEGENDS

Figure 1:
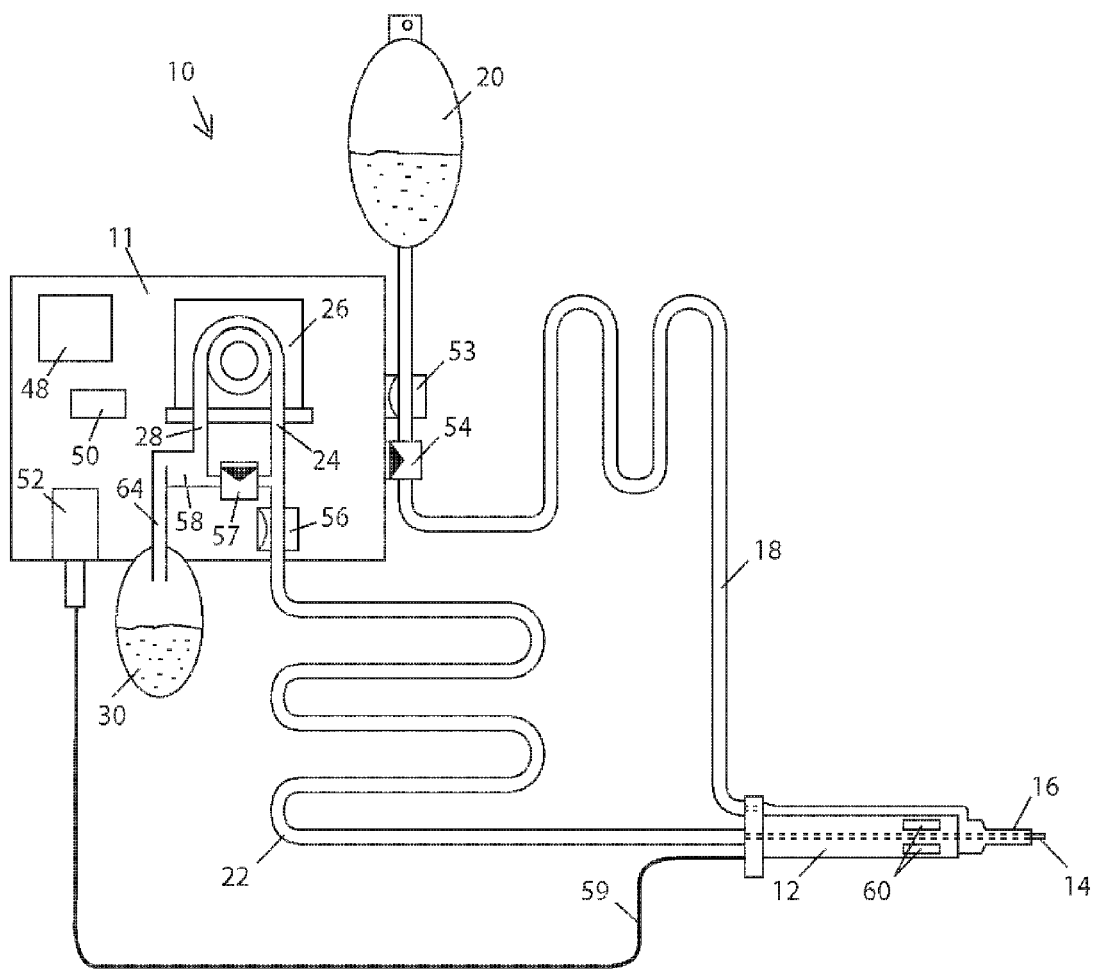
FIG. 1 is an illustration of a typical prior art lensectomy system.

10 prior art lensectomy surgical system,
11 console,
12 hand piece,
14 lensectomy probe,
16 infusion probe,
18 infusion/irrigation line,
20 infusion source,
21 aspiration line distal connector
22 aspiration line,
23 aspiration path,
24 pump input,
26 aspiration pump,
28 pump output,
30 waste fluid receptacle,
44 particle retaining filter,
48 user interface,
50 control module or CPU,
52 hand piece power driver,
53 irrigant pressure sensor,
54 infusion valve,
56 aspiration line vacuum sensor,
57 venting valve,
58 venting liquid deposit,
59 hand piece power cable,
60 hand piece power actuator,
64 waste fluid channel,
66 venting valve cable,
82 infusion valve cable,
84 irrigant pressure sensor cable,
86 aspiration pump control cable,
88 aspiration line vacuum sensor cable,
90 user interface cable,
94 miniature incision,
210 lensectomy surgical system,
270 normally-open occlusion valve,
272 occlusion valve cable,
274 actuator portion,
276 occlusion portion,
277 pinch valve,
278 collapsible elastic tubing segment,
280 in port,
282 out port,
284 plunger,
288 pivoting self-cleaning valve lid,
289 valve plunger with sharp "tissue chopping" edges,
290 compliance chamber,
299 valve bypass,
300 occlusion-break sensor,
310 occlusion-break sensor cable,
320 load cell,
330 collapsible elastic tubing segment,
335 diaphragm,
400 valve-and-sensor fixture,
410 valve-and-sensor fixture lid,
420 tubing guides,
425 lid latch,
510 vacuum sensor,
512 vacuum sensor signal cable,
520 distal common aspiration path,
522 low vacuum aspiration tubing,
524 low vacuum pump in-port,
526 low vacuum pump,
528 low vacuum pump out-port,
530 low vacuum pump waste fluid deposit,
564 low vacuum pump waste fluid tubing,
572 flow sustaining valve,
586 low vacuum pump driver signal carrier,
600 stand alone surge canceling system,
610 controller,
612 surgical hand piece,
622 aspiration line,
626 vacuum source,
630 vacuum sensor,
632 vacuum sensor signal carrier,
655 fluid source,
657 vacuum canceling valve,
658 vacuum canceling valve signal carrier,
659 three way connector,
670 blocking valve,
672 blocking valve signal carrier,
700 dual pneumatic pinch valve,
710 normally closed valve portion,
712 normally closed portion in-port,
714 normally closed portion out-port,
716 valve plunger,
718 air chamber,
720 diaphragm,
722 actuator body,
724 compression spring,
726 air port, 728 normally open valve portion,
730 normally open portion in-port,
732 normally open portion out-port,
734 normally open pinch valve portion tubing,
736 normally closed pinch valve portion tubing,
750 proximal system portion,
751 vacuum source,
752 vacuum sensor,
754 normally open valve,
756 normally closed valve,
758 normally closed valve,
759 normally open valve,
760 fluid deposit,
762 first aspiration line,
763 venting line,
764 second aspiration line,
765 venting line,
766 valve array,
768 vacuum sensor,
770 vacuum sensor,
772 normally open valve,
774 normally closed valve,
850 three way pinch valve array (2 normally closed, 1 normally open),
900 vacuum canceling fluid source,
905 active volume injector,
910 fluid reservoir,
915 collapse actuator,
920 flow resistance,
925 collapsible chamber,
930 check valve,
950 injection system cable
960 bypass connection

DETAILED DESCRIPTION

Figure 4:
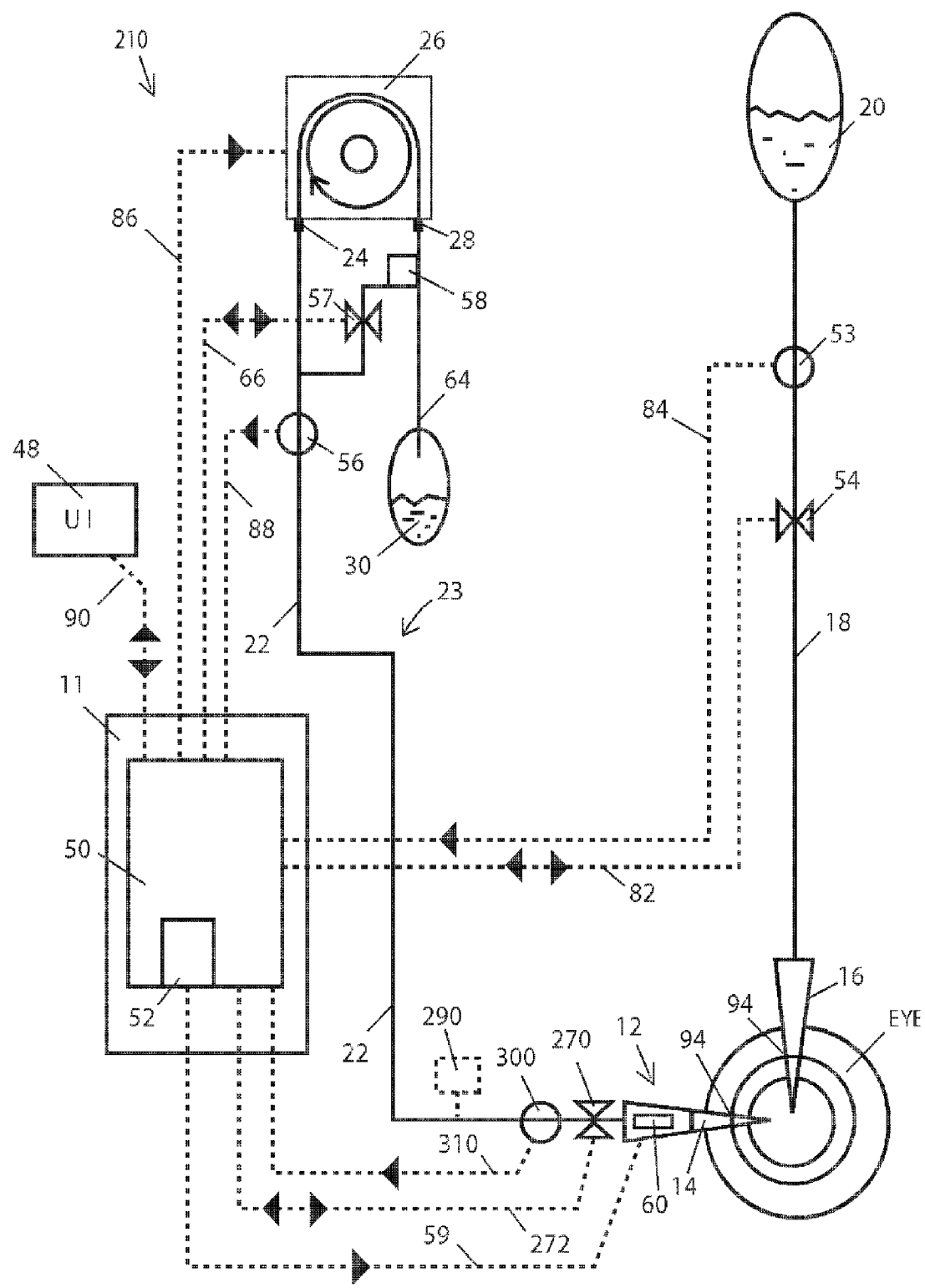
FIG. 4 is a schematic illustration of a preferred embodiment of the present invention.

As shown in the prior art FIG. 1, and also in FIG. 4, lensectomy surgical systems 10 for use through an operating hand piece 12 include a console 11. Console 11 generally includes a control module or CPU 50 providing control means, a vacuum source, e.g., aspiration pump 26 connected to CPU 50 through a cable 86 and a hand piece connected to power driver 52 and CPU 50 through a cable 59. An irrigant solution is contained in an infusion source 20 being fed into an eye chamber with a pressure typically set by gravity or a source of compressed gas. Hollow probe 14 and infusion probe 16 typically operate inserted into an eye chamber through one or more tight incisions 94. An infusion valve 54 can deliver irrigant solution through an infusion line 18 and infusion probe 16 into the eye under operator command through a user interface 48 typically including a foot pedal (or related operator input device of which a foot pedal is a non-limiting example). Infusion valve 54 is connected to CPU 50 through a cable 82. Cable 82 can also provide a valve 54 status signal back to control module 50.

An irrigant pressure sensor 53 is operably connected to irrigation line 18 at console 11 to inform control module 50 about pressure of the irrigant solution through a cable 84. Fluid and tissue fragments can be aspirated from inside the eye by a vacuum force produced by aspiration pump 26 which is in fluid communication with the eye chamber through an aspiration line 22, hand piece 12 and hollow lensectomy probe 14. Vacuum inside aspiration line 22 is monitored using a vacuum sensor 56 usually located at console 11 and connected through a cable 88 to control module 50.

Fluid is aspirated into pump 26 through a pump input 24 and exits pump 26 as waste fluid through a pump output 28 across a waste fluid channel 64 into a waste fluid receptacle 30. The aspiration system described above includes an aspiration path 23 conformed by the aspiration fluid channel determined in sequence through lensectomy probe 14, hand piece 12, aspiration line tubing 22 and pump input 24. Pump 26 is typically a peristaltic or Venturi pump. When using a Venturi pump, waste receptacle 30 is typically located between aspiration line 22 and pump input 24, and air "fluid" is employed as well as liquid fluids in a manner that is customary for a Venturi pump.

An operator can instruct CPU 50 through user interface 48 to activate a power driver 52 to apply power to power actuators 60 inside hand piece 12 through a power cable 59. The energized actuators 60 transmit energy to hollow probe 14 delivering a lens tissue-disruptive energy to disrupt the lens tissue allowing aspiration through the distal opening of hollow probe 14.

A venting liquid deposit 58 holds irrigant derived from pump output 28 that can serve as a source of venting fluid for a venting valve 57 actuated by control module 50 through a cable 66. Cable 66 can also provide a venting valve 57 status signal back to control module 50. Venting valve 57 provides aspiration line vacuum relieving means usually by opening temporarily to relieve an eventual vacuum inside aspiration path 23 after cycles of aspiration.

Deposit 58 is typically at atmospheric pressure but a pressurized source of venting fluid, preferably liquid, can also be implemented. User interface 48 operation typically includes a sequence of at least four distinctive command positions usually using a foot pedal as the input device. Position 0 is idle, 1 is only irrigation delivered to the eye, 2 is irrigation and aspiration, 3 is irrigation, aspiration and disruptive energy applied to tissues through hollow probe 14 inside the eye. Prior art system 10 may be a commercially available surgical console such as the Infiniti Surgical System from Alcon Laboratories, USA. Control module or CPU 50 may be any suitable microprocessor, micro-controller, computer or signal processor. Control module or CPU 50 exchanges data signals with user interface 48 through connector 90. A power driver 52 is incorporated into control module 50.

The post-occlusion chamber collapse canceling system for a surgical apparatus of the present invention incorporates the elements described above for the prior art system illustrated in FIG. 1, as well as in FIG. 4.

Figure 2:
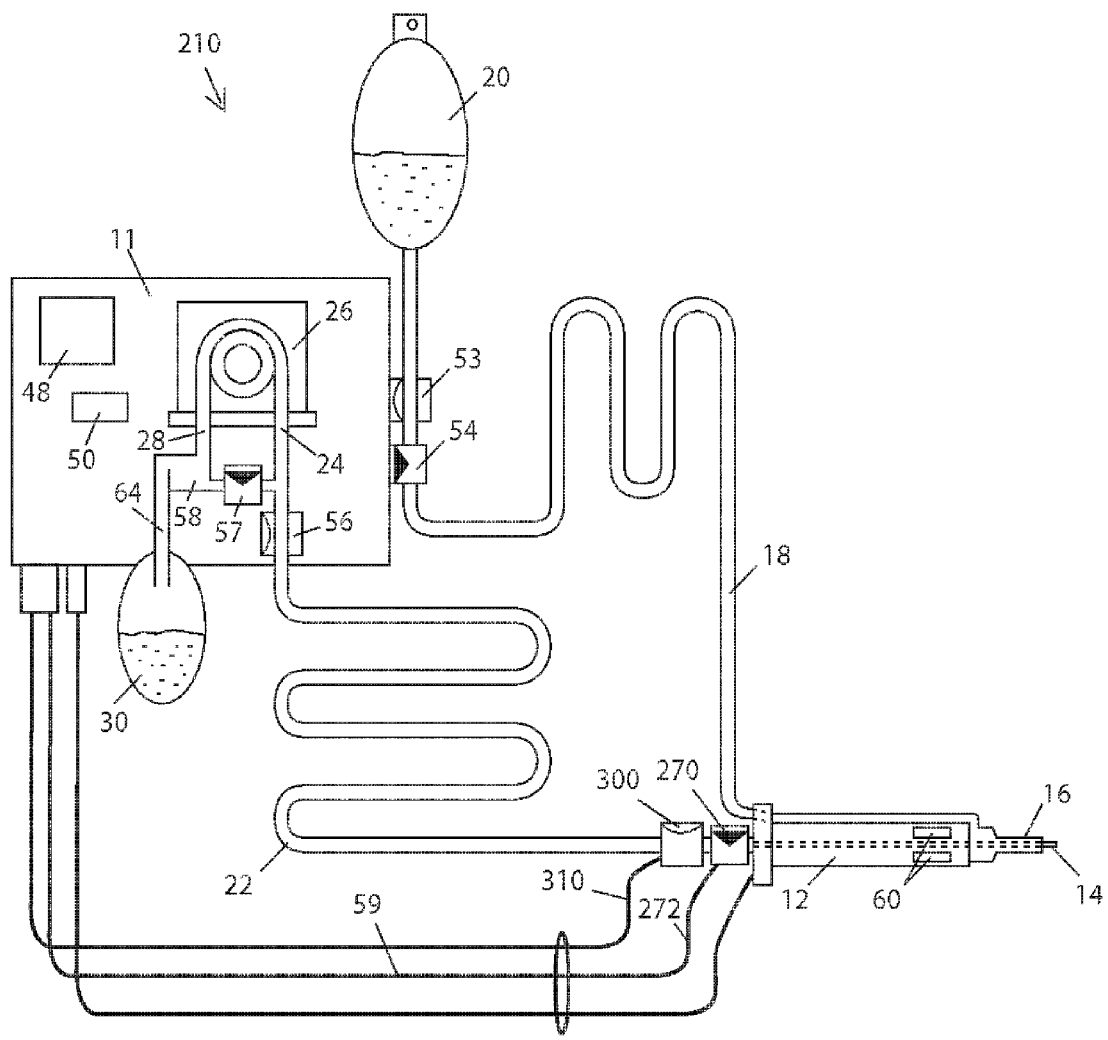
FIG. 2 is an illustration of one embodiment of the lensectomy system of the present invention.
Figure 10A:
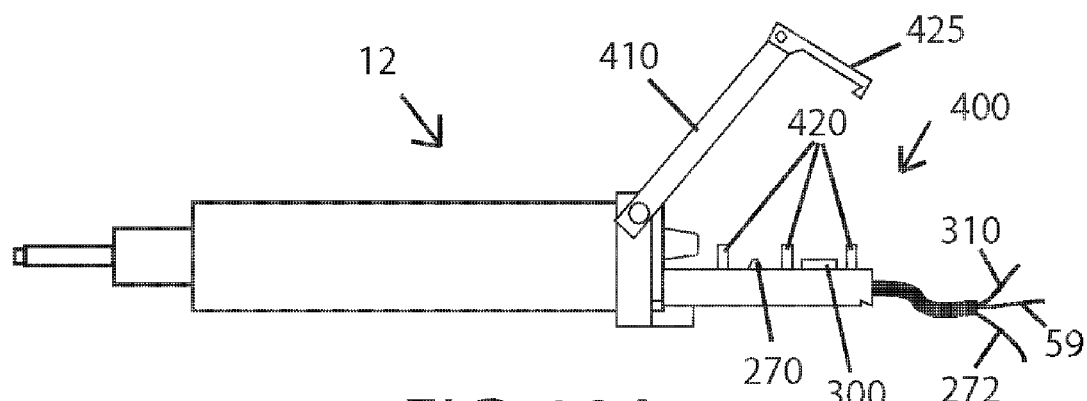
FIG. 10A illustrates a side view of a fixture that can hold an aspiration line blocking system and an aspiration line occlusion-break sensing device shown with the lid open and tubing detached.
Figure 10B:
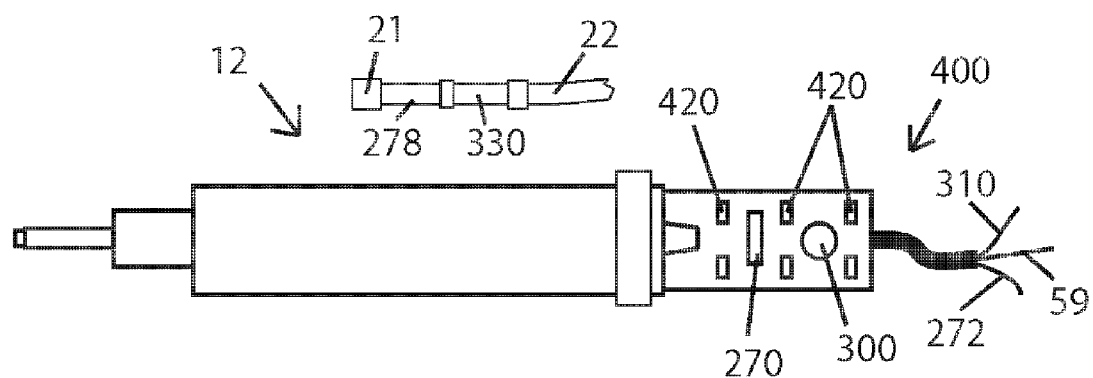
FIG. 10B illustrates a top view of the fixture from FIG. 10A shown here with the lid removed and tubing detached.
Figure 10C:
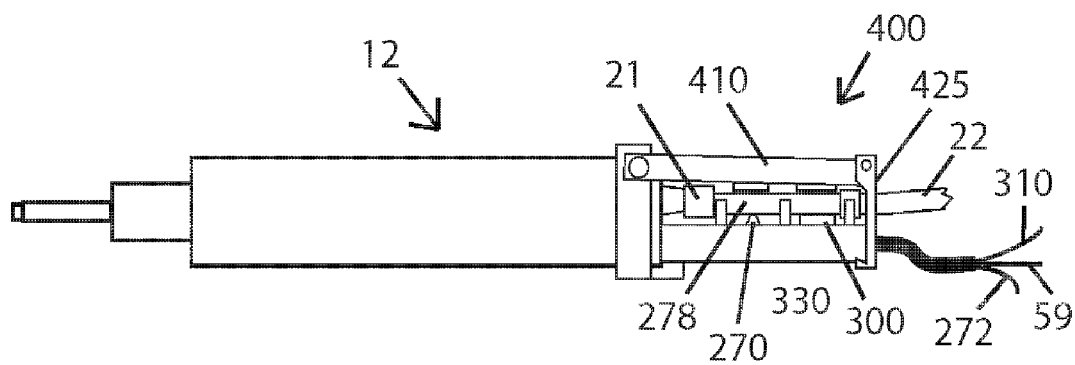
FIG. 10C illustrates a side view of the fixture from FIG. 10A shown here with the lid closed and tubing attached ready for operation.

Now turning to FIGS. 2 and 4, the post-occlusion chamber collapse canceling system of the present invention 210 further incorporates a) a normally-open occlusion valve 270 that provides aspiration line occluding means and b) an occlusion-break sensor 300 that provides occlusion-break detecting means. Normally-open occlusion valve 270 receives commands from control module 50 through a cable 272. Cable 272 can also provide a valve 270 status signal back to control module 50 for safe operation. As shown in FIGS. 6A and 6B, normally-open occlusion valve 270 can have an actuator portion 274 and an occlusion portion 276. For maximum efficiency, normally-open occlusion valve 270 should be located at the distal end of aspiration path 23, as near as possible to the eye, see FIGS. 2, 3, 4, 5, 12, 13, 18, 20A, which all illustrate the manner in which normally-open occlusion valve 270 is located proximate the distal end of the aspiration path. This distal proximity of normally-open occlusion valve 270, in practice, will motivate installation in close proximity to hand piece 12, or inside hand piece 12. A preferred embodiment shown in FIG. 10 is shows a distal location where normally-open occlusion valve 270 is split, having actuator portion 274 attached to or incorporated in hand piece 12 and having occlusion portion 276 as part of the distal end of aspiration line 22. In this configuration, functionality of normally-open occlusion valve 270 is achieved when aspiration line 22 is connected to hand piece 12 by a detachable connector 21. This embodiment is advantageous because it allows having a disposable low cost occlusion portion 276 operating in combination with a non-disposable actuator portion 274.

FIG. 6A depicts normally-open occlusion valve 270 in the form of a pinch valve 277 shown in open condition. Plunger 284 is retracted allowing the lumen of collapsible elastic tubing segment 278 to remain patent. An in port 280 receives the irrigant solution together with (unnumbered) tissue fragments aspirated from inside the eye. The fluid and solid particles traverse tubing 278 with negligible resistance and exit out port 282 toward aspiration pump 26. FIG. 6B depicts pinch valve 277 in closed condition. Plunger 284 is protracted closing the lumen of collapsible elastic tubing segment 278, blocking aspiration path 23. In this condition, fluid and solid particles cannot traverse tubing 278. The pinch valve 277 should be self cleaning on reopening, and thereby immune to clogging produced by tissue fragments aspirated from the surgical site. In the event a non-self cleaning occlusion valve is selected, a particle retaining filter should be inserted upstream to avoid clogging, see, e.g., the particle retaining filter in FIG. 7A. Pinch valve 277 is a suitable selection for normally-open occlusion valve 270 because of speed of operation (tens of millisecond or less), non-clogging operation with liquids containing solid particles (tissue fragments), bidirectional flow and reliability. Pinch valve 277 actuator portion 274 can be a solenoid, an electromagnet, a linear actuator, a piezoelectric actuator, a piezoelectric motor or any other power source capable of temporarily pinching a segment of collapsible elastic tubing 278. Considerations such as weight, speed, reliability, resistance to sterilization and cost can influence the selection of the kind of valve actuator 274 depending on particular implementations of this invention. Solenoid-driven pinch valve Model 390-NO-12-330 from ASCO Scientific, USA serves as a non-limiting example of the type of valve which can be used as normally-open occlusion valve 270 in the present invention. This valve is designed as a two way normally-open pinch valve for a 1.6 mm inner diameter tubing. A pulse-and-hold feature can be incorporated in the driving electronics of the solenoid to reduce heat generation, allowing the selection of lighter and smaller coils for the task of pinching the elastic tubing.

Turning back to FIG. 10, a valve-and-sensor fixture 400 can be implemented to accommodate normally-open occlusion valve 270 in a way that tubing 278 can be removably attached, for example as part of a disposable tubing set. In general aspiration line 22 should be made of a flexible material with a low contraction index under applied internal vacuum to allow faster response time of the present invention. A collapsible chamber 290 shown in FIG. 4 can be inserted to add compliance near the distal end of aspiration line 22 to enhance detection of occlusion-break events. When occlusion breaks, chamber 290 rapidly expands increasing the rate of pressure drop, increasing the sensitivity and response time of occlusion-break detector sensor 300.

The segment of collapsible elastic tubing 278 introduced for operation of pinch valve 277 should have the smallest allowable length not to degrade performance. An 8 mm segment of silicone tubing with an inner diameter of 1.6 mm and outer diameter of 3.2 mm has operated well while experimentally testing this invention. Other forms of occlusion valves can be considered.

Figure 7A:
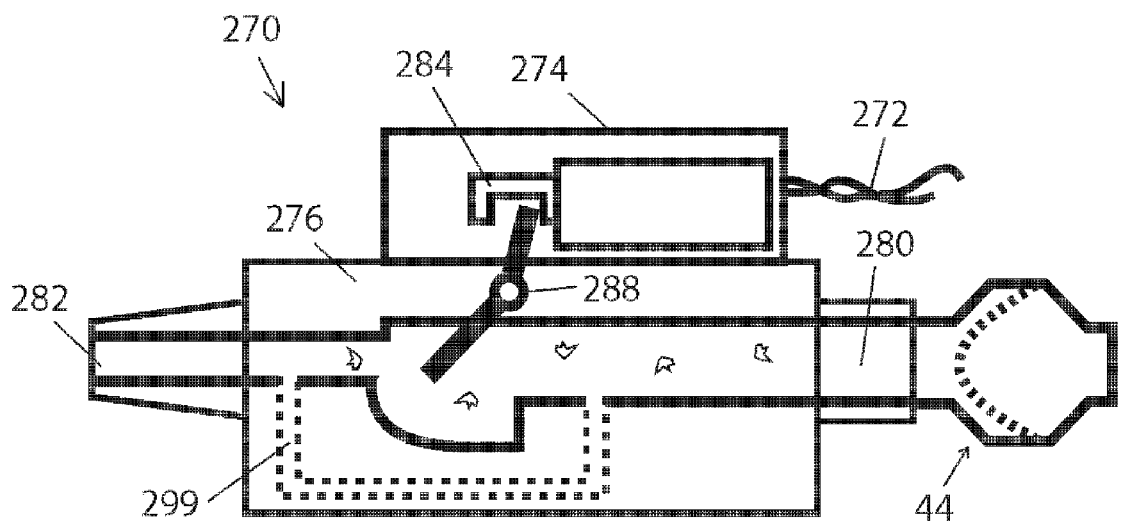
FIG. 7A is an illustration of another embodiment for an aspiration line blocking system shown in open condition.
Figure 7B:
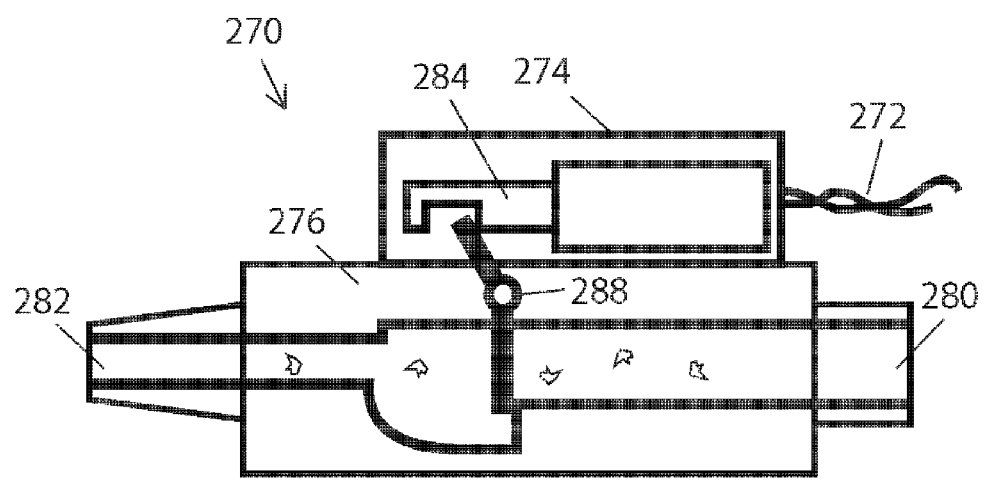
FIG. 7B is an illustration of the embodiment of FIG. 7A for an aspiration line blocking system shown in closed condition.

Depicted in FIGS. 7A and 7B is an alternative normally-open occlusion valve 270 shown in FIG. 7A in open position and in FIG. 7B in closed position. FIG. 7A also illustrates an optional valve bypass 299 and optional particles retaining filter 44 to be discussed later. This embodiment of normally-open occlusion valve 270 has an input 280 and an output 282. An actuator portion 274 with solenoid 284 can be detachably coupled to operate pivoting lid 288 located in an eventually disposable occlusion portion 276 part of a tubing set. Design of the fluid path within valve 270 and of pivoting lid 288 avoids clogging by tissue fragments. It is possible to configure normally-open occlusion valve 270 in a chopper-valve configuration using a guillotine-like valve lid. In this modality tissue fragments traversing the valve during closure are segmented avoiding valve dysfunction and clogging. Many other options exist to regulate flow besides the ON-OFF valves illustrated here, such as proportional valves also suitable for practicing this invention.

Figure 25A:
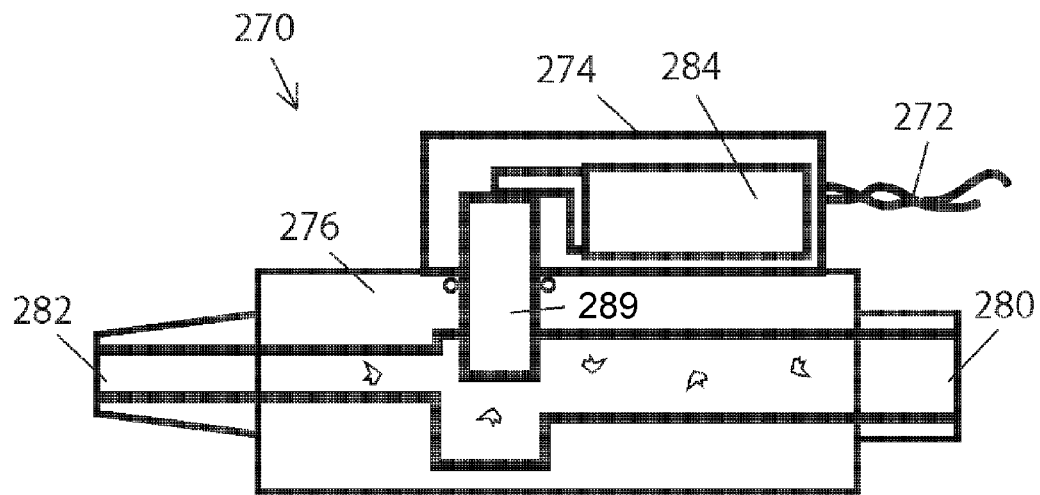
FIG. 25A is an illustration of another embodiment for an aspiration line blocking system shown in open condition, including a "tissue chopping" operation.
Figure 25B:
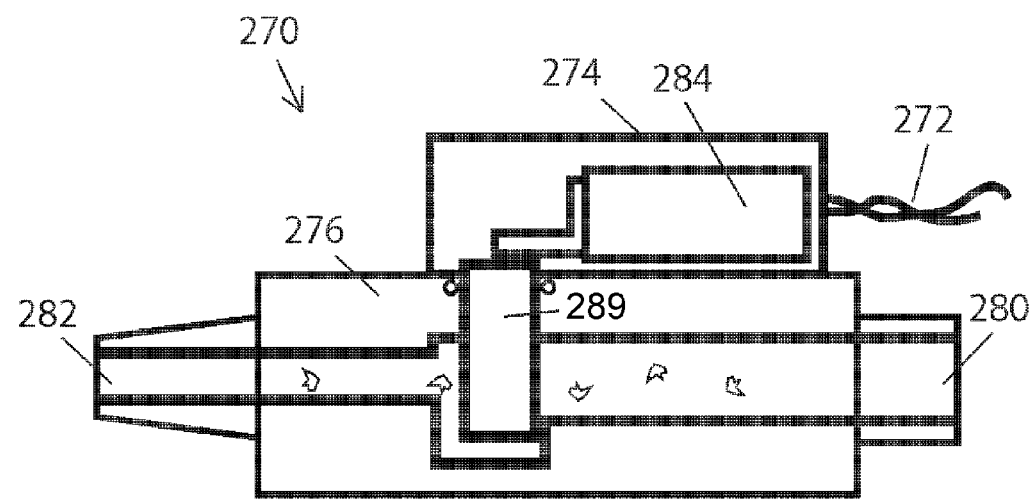
FIG. 25B is an illustration of the embodiment of FIG. 25A, shown in closed condition.

Depicted in FIGS. 25A and 25B is an alternative normally-open occlusion valve 270, shown in FIG. 25A in open position and in FIG. 25B in closed position, further illustrating this guillotine-like "chopper valve" lid. This embodiment of normally-open occlusion valve 270 has an input 280 and an output 282. A rotary or linear actuator portion 274 with solenoid 284 can be detachably coupled to operate a plunger 289 located in an eventually disposable occlusion portion 276 part of a tubing set. Plunger 289 can have sharp edges in a way that tissue fragments interposed in the plunger path during operation are segmented. This guillotine-like valve embodiment configures normally-open occlusion valve 270 in a "tissue-chopper" valve modality avoiding valve malfunction and clogging caused by tissue fragments aspirated from the eye chamber.

Occlusion-break sensor 300 provides an electric signal to control module 50 through cable 310 indicating that an occlusion-break event has occurred. In a preferred embodiment, occlusion-break sensor 300 comprises a vacuum sensor installed in the aspiration system, and as noted above, collapsible chamber 290 shown in FIG. 4 can be used to enhance the sensitivity and response time of occlusion-break detector sensor 300.

Operation of many of the invention embodiment disclosed here, is based on the fact that after an occlusion-break event occurs, there is a rapid drop in vacuum in the aspiration system. The rate of change of pressure dP/dt provides information about the timing and about the prospective magnitude of the post-occlusion surge being detected. Control module 50 can use the onset and the magnitude of the dP/dt signal provided by sensor 300 to compute the beginning and duration of the chamber collapse canceling response. The faster an occlusion-break event can be detected, the faster the compensating actions can be started, thereby improving performance.

Experimentally practicing this invention has taught that the location of sensor 300 is determinant in the delay observed between the actual occlusion break and the detection signal provided by sensor 300, and therefore, in the overall effectiveness of the surgical system When using a dP/dt sensor as sensor 300 installed in aspiration path 23, the response time increases with increasing distance between the site of occlusion break and sensor 300 location. Installing occlusion-break sensor 300 inside hand piece 12 or at the distal portion of aspiration line 22 rendered optimum results. In a preferred embodiment shown in FIG. 8, occlusion-break detector 300 uses a load cell 320 and tubing 330, and is operable to provide a dP/dt signal. Load cell ELMF-B1-25N from Measurement Specialties, USA serves as an example of a load cell suitable for practicing this embodiment of occlusion-break detector 300.

Shown in FIG. 10 is a valve-and-sensor fixture 400 that can include sensor 300 and pinch valve 270. Valve 300 can be in the form of load cell 320 approximately perpendicularly-adjusted and slightly compressing the walls of a segment of elastic collapsible tubing 330 inserted near the distal end of aspiration path 23. Fixture 400 can have a hinged lid 410 incorporating a locking latch 425 and tubing guides 420. In this way tubing portions 278 for pinch valve 270 and 330 for occlusion-break detection together with aspiration line 22 distal connector 21 can be detachably coupled to hand piece 12.

Fixture 400 forms a valve-and-sensor fixture that can be a stand-alone unit or can be integrated into a surgical hand piece 12. Collapsible tubing 330 is selected to preserve a patent fluid channel and remain in effective contact with load cell 320 across the full range of vacuum levels produced by aspiration pump 26. The minimum possible inner diameter of tubing 330 should preferably be above 1.5 mm to avoid clogging by solid particles. A silicone tubing segment of about 8 mm having 3.2 mm ID and 4.8 mm OD has been shown during experimental testing to be operative for practicing this invention. Fluctuations in pressure inside the lumen of tubing 330 which are typical of occlusion-break events produce an expansion of the walls of tubing segment 330 exerting a force over load cell 320 that is a function of vacuum at that location. Load cell 320 produces an electrical signal that is proportional to the force detected from tubing 330 walls. This signal is transmitted across cable 310 to control module 50 for processing.

One advantage of using this load cell and elastic tubing approach for occlusion-break sensor 300 is that the more expensive load cell can be integrated into a non-disposable element fixture 400 or hand piece 12, while the inexpensive elastic tubing can be integrated into a disposable tubing set. Alternatively to tubing segment 330 and for improved performance, a differentiated portion including an elastic element such as a chamber with elastic walls can be designed to get in contact with load cell 320 such as a bellows region or a diaphragm region to transmit a force to load cell 320 that is a function of the vacuum in aspiration path 23.

In general terms, sensor 300 must be accurate to detect the timing of the occlusion-break event, but not necessarily accurate to provide a proportional signal to dP/dt. This because aspiration line vacuum sensor 56 is typically well-calibrated and can complement vacuum information for control module 50. Other kinds of sensors capable of timely detecting the occlusion-break events can be used, such as dP/dt sensors, pressure sensors, position sensors, acceleration sensors, thermal dilution flow sensors, ultrasonic flow sensors. These sensors can be installed in the distal portion of aspiration path 23 to operate as occlusion-break detector 300, the output signal being converted to an estimated dP/dt value using electronic or digital differentiating means.

Alternatively, occlusion sensor 300 can only provide a digital ON-OFF output signaling the occurrence of an occlusion break to control module 50, and the vacuum at occlusion break onset information can be extracted from aspiration line vacuum sensor 56. The ON-OFF signal can be triggered for example when a dP/dt threshold value is detected by sensor 300. Occlusion-break events also propagate a pressure wave upstream into irrigation line 18. For this reason sensor 300 in the form of a dP/dt sensor could be installed in irrigation line 18 although during testing, this approach proved less reliable and with increased response time.

Figure 12:
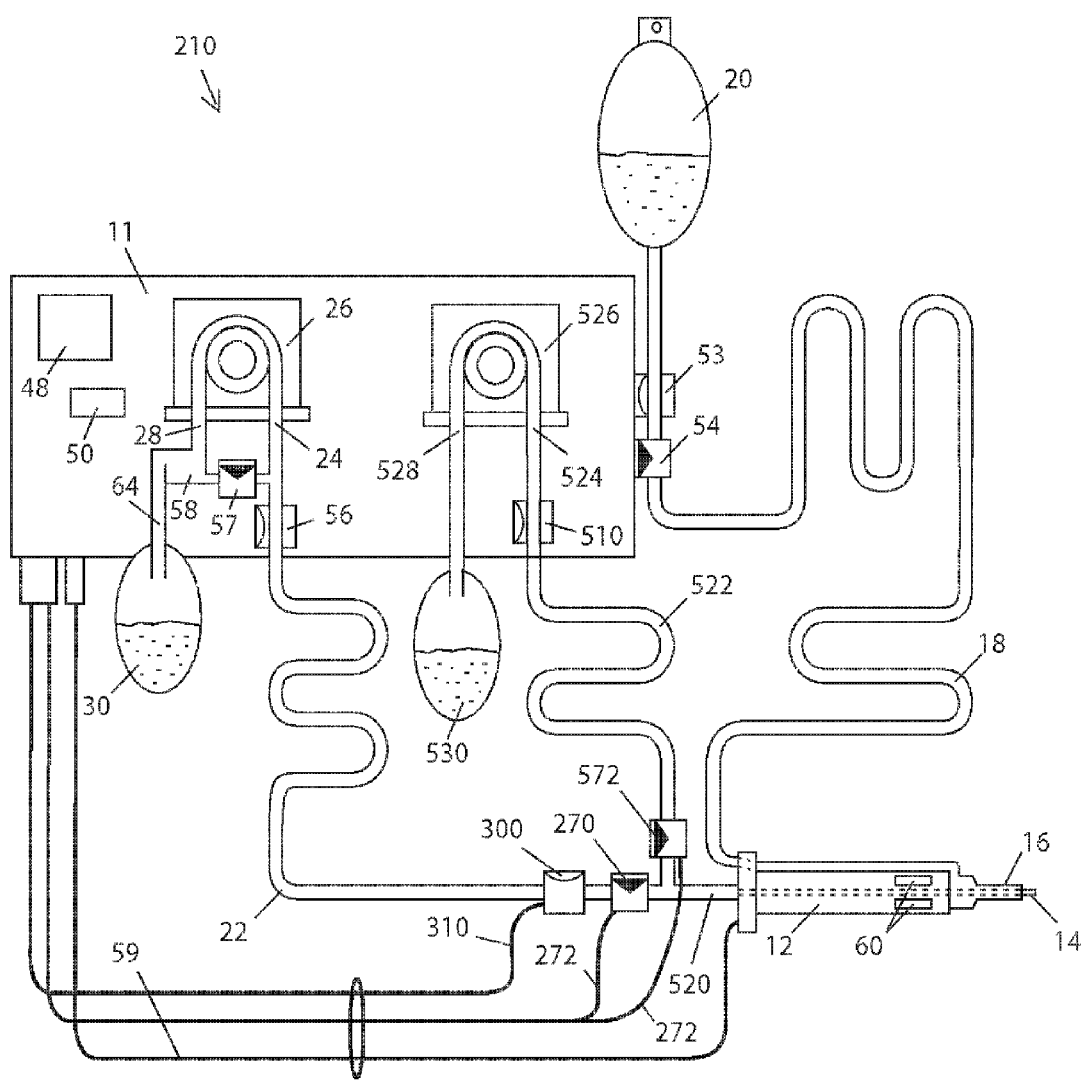
FIG. 12 is an illustration of another embodiment of the lensectomy system of the present invention.
Figure 13:
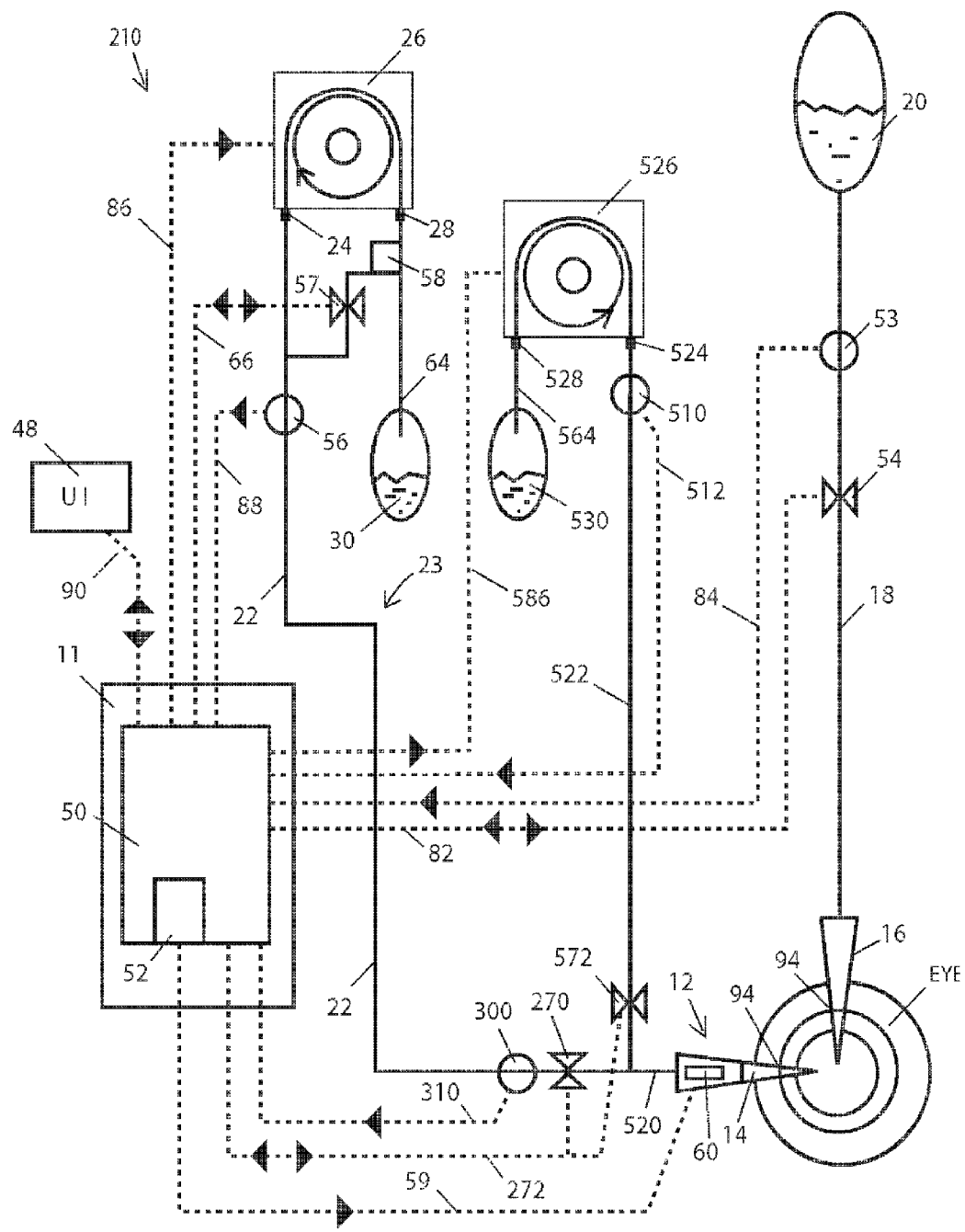
FIG. 13 is a schematic illustration of the embodiment shown in FIG. 12.

An alternative embodiment depicted in FIG. 12 and FIG. 13 further incorporates a second valve 572 in normally-closed position. Valve 572 can be connected to driver signal carrier 272 driving normally-open valve 270. Valve 572 is in fluid communication with a portion 520 of aspiration path 22 located between lensectomy probe 14 and valve 270. Valve 572 opposite port is in fluid communication through a tubing 522 with a source of vacuum 526 though a vacuum in-port 524. An optional vacuum sensor 510 can be installed in the aspiration path between valve 572 and vacuum source 526 and connected to controller 50 through a sensor 510 signal carrier 512. Pump 526 is operated by controller 50 through a driver signal conducted through a signal carrier 586. Fluid aspirated into pump 526 exits through a pump out-port 528 across a fluid path 564 into a waste fluid collector 530. Vacuum source 526 is illustrated as a peristaltic pump but other vacuum sources such as Venturi pumps or gravity can be employed. Also, line 522 can be connected to a receptacle at atmospheric pressure instead to a vacuum source. Vacuum source 526 can provide structure or methods to cancel vacuum inside aspiration line 522 such as shown for pump 26 with fluid deposit 58 and vacuum-canceling, venting valve 57. Also stopped and/or reversed and/or reduced pump operation can be used to reduce vacuum when valve 572 is in closed condition.

Figure 14A:
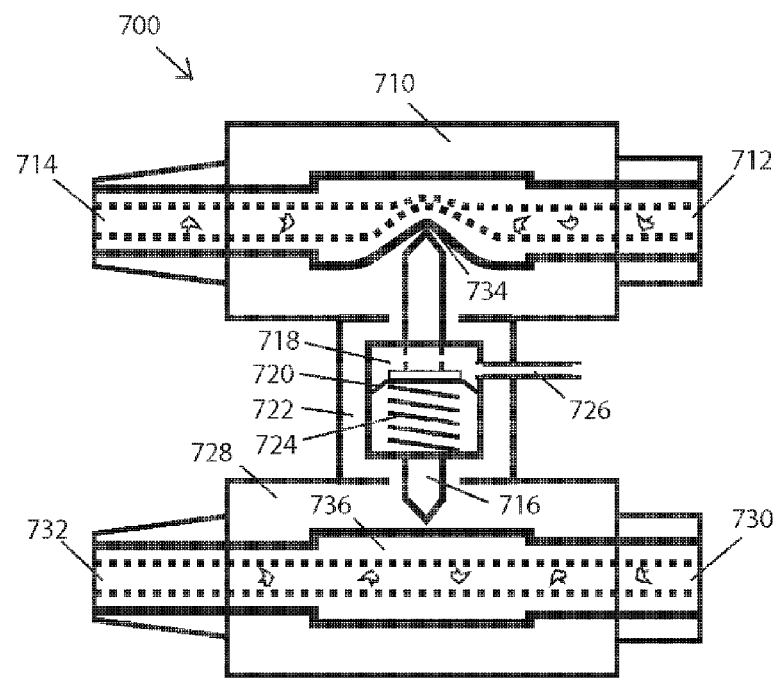
FIG. 14A is an illustration of an alternative embodiment for an aspiration line blocking system further incorporating a second normally closed valve portion shown in resting condition.
Figure 14B:
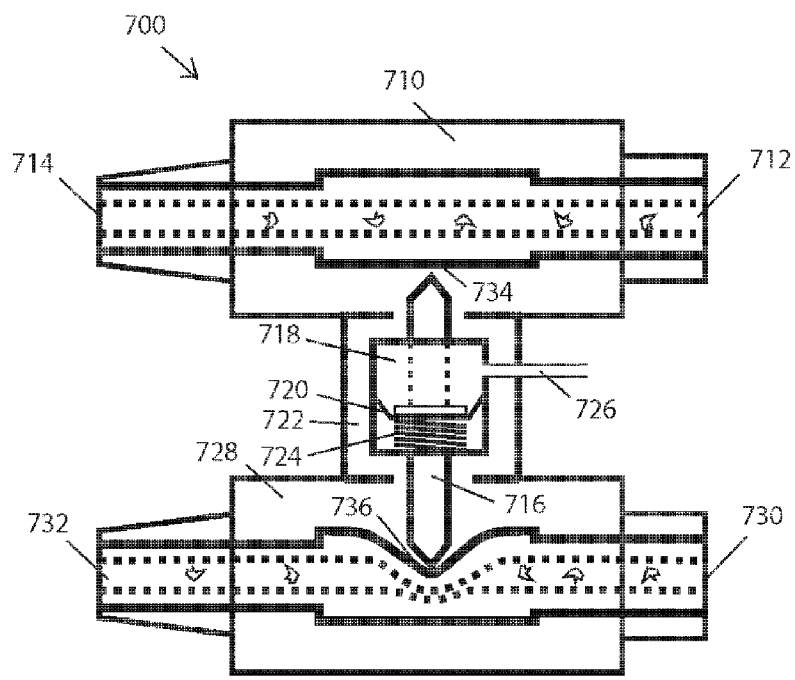
FIG. 14B is an illustration of the alternative embodiment for an aspiration line blocking system shown in FIG. 14A shown in active condition.

This embodiment in which normally open valve 270 and normally closed valve 572 are combined in a single two-way valve operates as follows: An electrically-operated two-way valve meeting the specifications for the purposes of this invention can be similar to pinch valve part No. 225P091-21 from NResearch, USA. Alternatively, as depicted in FIG. 14A and FIG. 14B a pneumatically operated two-way valve 700 can be implemented for disposability and weight considerations. In this condition signal carrier 272 for valves 270 and 572 corresponds to a pressurized air tubing conducting pressurized air from a pressurized air source activated under controller 50 command. The same condition applies in an embodiment where only valve 270 is present. FIG. 14A shows dual pneumatic pinch valve 700 in inactive condition. A normally closed valve portion 710 has a normally open pinch valve tubing 734 with an in-port 712 and an out-port 714. A normally open valve portion 728 has a normally closed pinch valve tubing 736 with an in-port 730 and an out-port 732. Both in-ports 712 and 730 are in fluid communication with hollow lensectomy probe 14 through a distal common aspiration path 520. Out-port 714 is connected to low vacuum source 526 through tubing 522. Out-port 732 is connected to high vacuum source 26 through tubing 22. A plunger 716 is pressed against and blocks pinch tubing 734 by the force exerted by a compression spring 724. Air port 726 can admit compressed air from a pressurized air source provided by console 11 or a stand-alone surge canceling module 600, see FIG. 17, into an air chamber 718. A diaphragm 720 is disposed to seal air-chamber 718 around plunger 716 in a valve body 722. In operation, compressed air provided into air chamber 718 neutralizes the force of spring 724 compressing it to a point in which the blocking force exerted to pinch tubing 734 is relieved opening valve portion 710. Simultaneously, plunger 716 exerts a force over tubing 736 producing a pinching and blocking effect of valve portion 728. This active condition is depicted in FIG. 14B. In this manner, after there is an occlusion break, the closing of normally open valve 270 together with the opening of normally closed valve 572 serves to mitigate the post-occlusion surge of the vacuum into the eye through handpiece 12, by both blocking the high vacuum source (closing normally open valve 270) and connecting with a lower vacuum source (opening normally closed valve 572) to maintain an outflow. Through this exemplary, non-limiting embodiment, one achieves a physical connection between a second normally-closed venting valve 572 and the normally-open occlusion valve 270, wherein, as a consequence thereof, the opening of the second normally-closed venting valve 572 and the closing of the normally-open occlusion valve 270 occurs substantially simultaneously. and the closing of the second normally-closed venting valve 572 and the opening of the normally-open occlusion valve 270 occurs substantially simultaneously. This is not, however, limited to only valves 572 and 270, but can be applied to any circumstance wherein it is desired to have a normally-open and a normally-closed valve switch between their normal default states and their opposite states in a substantially-synchronized manner.

Control module 50 or a stand-alone module 600 can include a microprocessor 610 with analog and digital input-output capabilities such as PIC 18F4520, Microchip, USA. Discrete element circuits are provided in FIG. 15 and FIG. 16 illustrating functional diagrams that can have equivalent operation within the scope of this disclosure and its associated claims, using a processor 610 executing a computer program.

Figure 15:
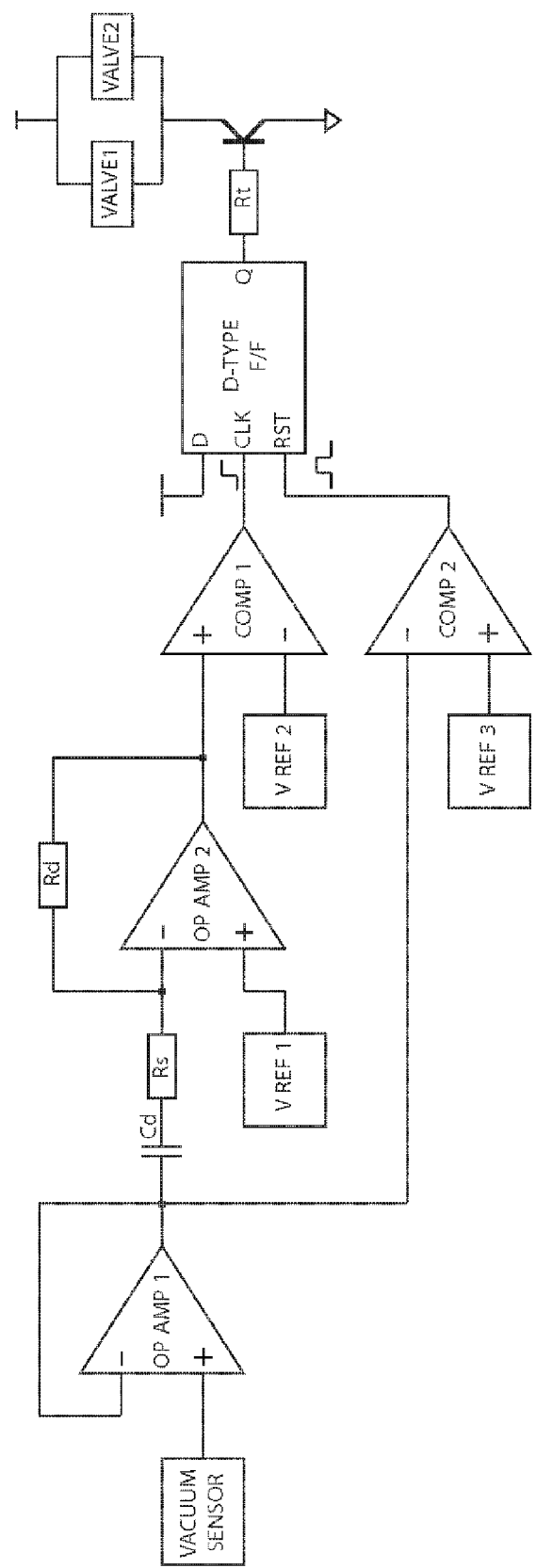
FIG. 15 illustrates a basic schematic circuit for a controller system for the present invention using a feedback loop.

FIG. 15 depicts a circuit of a preferred embodiment operating in servo control mode using a vacuum signal for a feedback loop, though the specific circuit illustrated is exemplary, not limiting. A vacuum sensor such as MPXV4115VC6U from Freescale Semiconductors, USA provides an output voltage proportional to the vacuum in aspiration line 22. This vacuum signal is buffered using OP AMP 1 used in voltage follower configuration. The output signal from OP AMP 1 is fed to a differentiator circuit mainly comprising Cd, Rd, V REF 1 and OP AMP 2. The output from OP AMP 2 provides a dVac/dt signal (change of Vacuum over time) following the equation Vout=−RC (dV/dt). Resistor Rs is placed for signal stability purposes and its influence is omitted from the equation on purpose. The output signal from OP AMP 2 is fed to a voltage comparator COMP 1 that will produce a positive square wave every time the dVac/dt signal is above a threshold voltage determined by a reference voltage V REF 2. The square signal produced by COMP 1 when dVac/dt is above a preset level is fed to the clock input CLK of a D-type flip/flop circuit, producing a change in the output stage Q that activates the blocking and vacuum canceling venting valves 270, 57, and flow sustaining valve 572 if implemented. The output signal from OP AMP 1 is also fed to a voltage comparator COMP 2 receiving a V REF 3 voltage reference signal. When vacuum level signal drops below a threshold value determined by V REF 3 then COMP 2 produces an output signal that is fed to the reset input RST of the flip/flop circuit, restoring the output Q to inactive status, ending the activation interval of venting valve 57, normally-open occlusion valve 270 and flow sustaining valve 572. In this way operation of the valves is initiated when the vacuum drops by an occlusion-break event and ends when vacuum inside aspiration line 22 has dropped by the vacuum canceling action of venting valve 57 to a predetermined low vacuum level set by adjusting V REF 2. A servo control with a feedback loop is thus established for operation in response to sensing that the danger of the vacuum surge has passed. In the specific, exemplary embodiment illustrated here, sensing that the danger of said vacuum surge has passed and returning the appropriate valve(s) to their default state is responsive to a signal of the feedback vacuum sensor.

Figure 16:
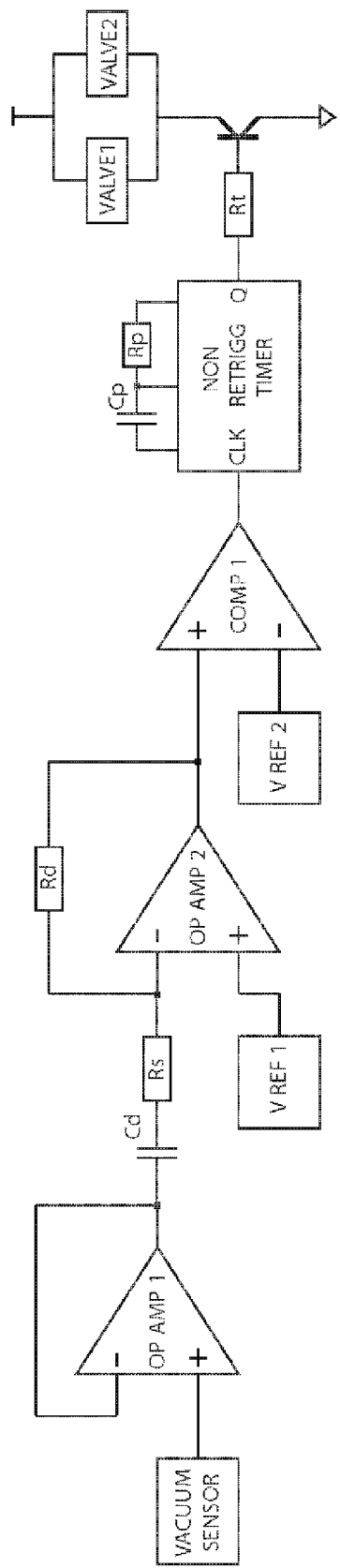
FIG. 16 illustrates a basic schematic circuit for a controller system for the present invention using a timer.

An alternative embodiment depicted in the circuit of FIG. 16, also exemplary, not limiting, corresponds to a timer based controller circuit 50 for a surge canceling system of the present invention. In this embodiment vacuum sensor 300 provides a voltage proportional to vacuum in aspiration path 23. Vacuum signal is buffered using OP AMP 1 used in voltage follower configuration. The output signal from OP AMP 1 is fed to a differentiator circuit composed by Cd, Rs, Rd, V REF 1 and OP AMP 2. The output from OP AMP 2 provides a dVac/dt signal (change of Vacuum over time) following the equation Vout=−RC (dV/dt). Resistor Rs is placed for signal stability purposes. The output signal from OP AMP 2 is fed to a voltage comparator COMP 1 that will produce a positive square wave every time the dVac/dt signal is above a threshold voltage determined by a reference voltage V REF 2. The square signal produced by COMP 1 when dVac/dt is above a preset level is fed to the clock input of a non-retrigerable monostable multivibrator such as 74HC221, producing a timed change in the output stage Q that transitorily activates venting valve 57, normally-open occlusion valve 270 and flow sustaining valve 572. The interval is determined by the values of Cp and Rp. In this way operation of said valves is initiated when the vacuum drops by an occlusion-break event and ends when the timed interval of activation of the monostable circuit has ended. This circuit provides a fixed aspiration line blocking and vacuum-canceling interval for all occlusion-break events with dVac/dt values above a preset level determined by V REF 1. More complex algorithms that incorporate i.e. the vacuum level just before the occlusion break occurs can be implemented by adding an analog or digital processor that modifies the timer output interval by adjusting the value of resistor Rp for example by using a programmable resistor such as MAX5471, Maxim, USA.

Figure 17:
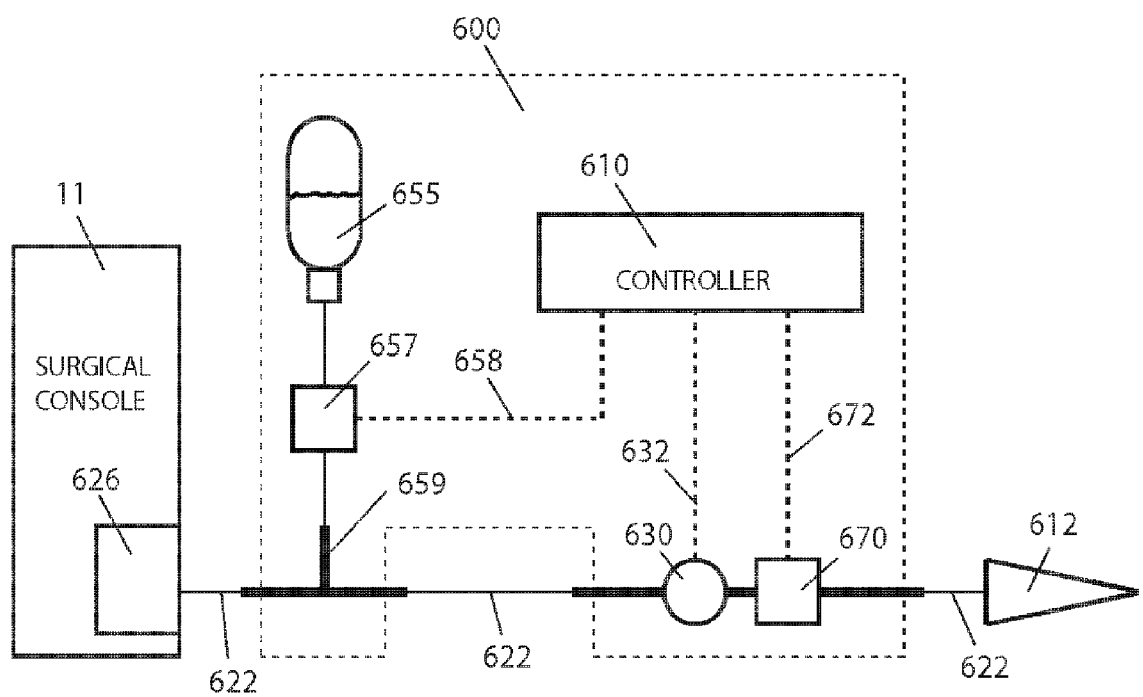
FIG. 17 is a schematic illustration of one embodiment of the present invention that can operate as a stand-alone unit in combination with a prior art surgical console.

The post-occlusion chamber collapse canceling system for a surgical apparatus of the present invention can be incorporated into a surgical console or, as depicted in FIG. 17, implemented as a stand-alone unit 600 to be used in conjunction with a pre-existing surgical console 11 having a vacuum source 626. In this retrofitting embodiment, a hand piece 612 is in fluid communication through an aspiration path 622 with vacuum source 626 integrated into a surgical console 11. The stand-alone unit can be installed in said surgical console 11 by incorporating a 3 way connector 659, a vacuum sensor 630 and a blocking valve 670 in aspiration path 622. Connector 659, sensor 630 and valve 670 can all be installed as a single array between the hand piece and an aspiration tubing upstream following aspiration path 622 without segmenting any tubing. Alternatively, sensor 630 and valve 670 can be inserted near the hand piece and T connector 659 can be inserted in aspiration path 622 proximal to console 626 by segmenting path 622 under sterile conditions. Connector 659 is also connected to a source of fluid 655 through a fluid path having a normally-closed valve 657 that can receive an activation signal from controller 610 through an activation signal carrier 658. As an option, venting fluid can be derived from irrigation line 18. Sensor 630 provides a vacuum signal to controller 610 through a signal carrier 632. Normally-open blocking valve 670 can receive an activation signal from controller 610. In operation, system 600 installed in the aspiration path of an existing surgical console operates by detecting the pressure drops that correspond to the occlusion-break events using sensor 630 and activates valves 670 and 657 to simultaneously block the surge and cancel the vacuum inside aspiration path 622 proximal to valve 622. Valve activation can be terminated using vacuum sensor based servo control or other computed interval algorithms.

Figure 18:
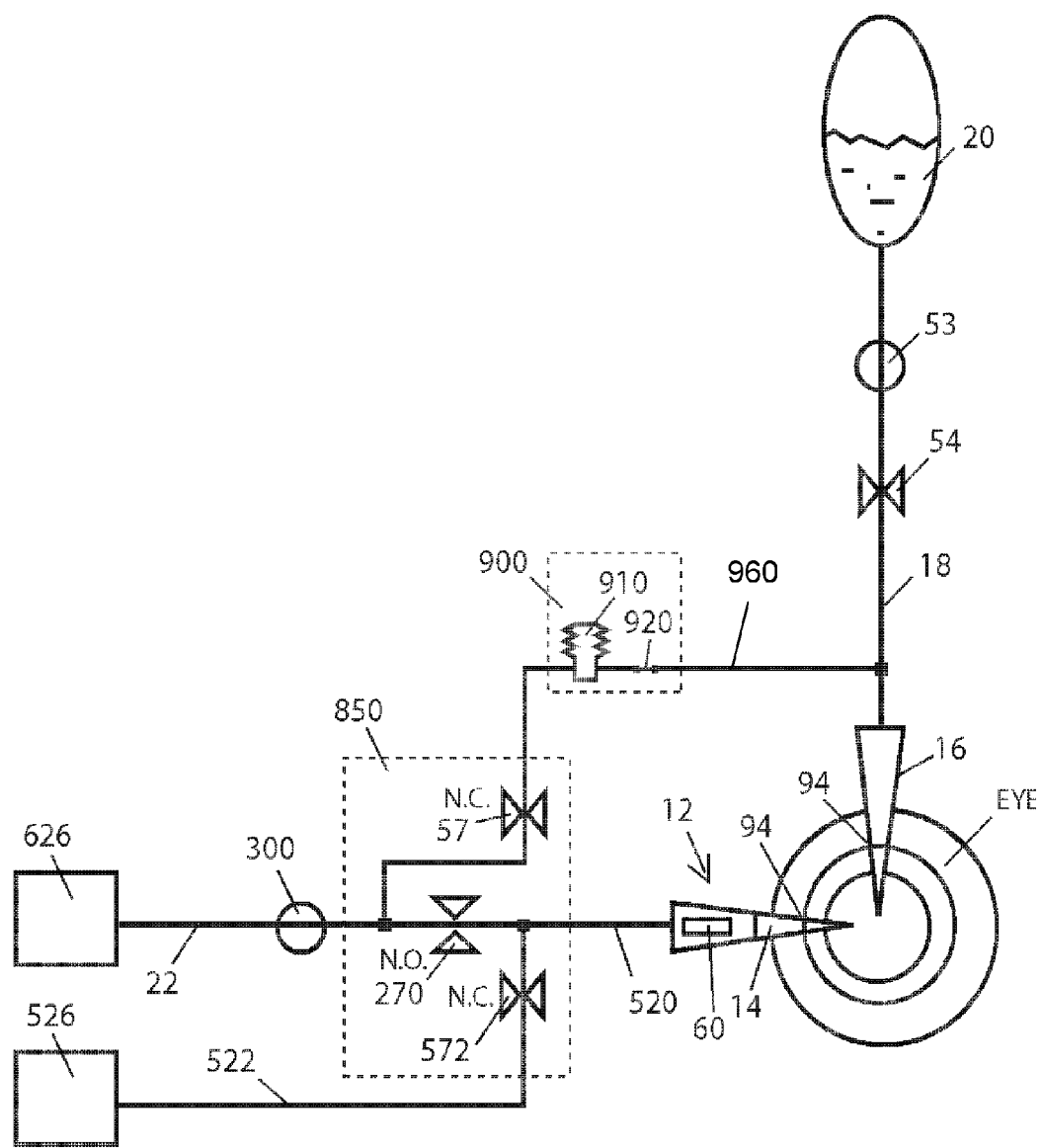
FIG. 18 is a schematic illustration of an embodiment that uses a valve array near the lensectomy probe and derives vacuum-canceling fluid from a buffer fed by the irrigation line.

FIG. 18 illustrates an embodiment employing a bypass connection 960 where normally open valve 270 and normally closed venting valve 57 are incorporated in a valve array 850. Valve array 850 can further include normally closed valve 572 if implementation of a second low vacuum source is considered. All valves can be driven by a single actuator electromagnetic or pneumatic actuator. An example of a valve array suitable to be used in this embodiment is the 4 way pinch valve part No. 360P071-21, from NResearch, USA.

Additionally, a vacuum-canceling fluid source 900 can consider a fluid deposit 910 connected to irrigation line 18 across an optional flow resistance 920. Fluid deposit 910 must be a low impedance source of fluid for venting valve 57. It can comprise a collapsible thin-walled chamber filled with liquid or alternatively it can be made of rigid walls optionally containing a portion of expansible compressed gas (air) to improve negative compliance. The volume readily available for vacuum canceling across venting valve 57 must preferably be in the range of 1.0 to 3.0 cc for each cycle of venting valve 57 activation. Deposit 910 is refilled with fluid derived from irrigation line 18.

Figure 21A:
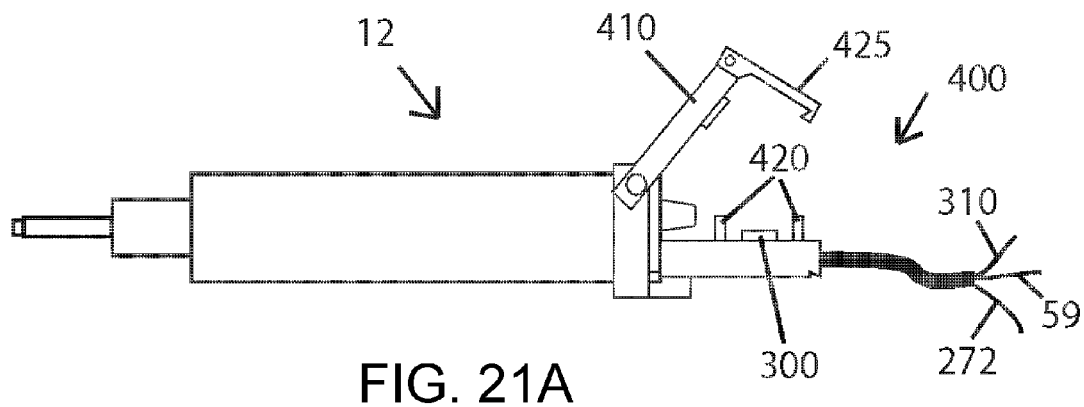
FIG. 21A illustrates a side view of a fixture that can hold an aspiration line occlusion-break sensing device shown with the lid open and tubing detached.
Figure 21B:
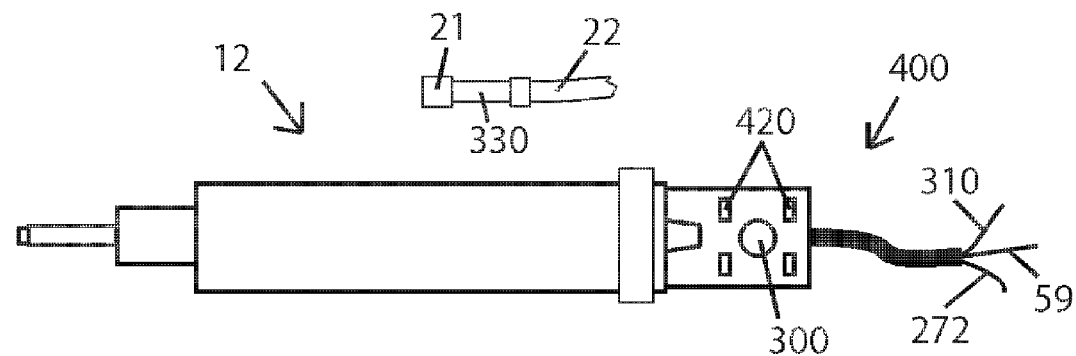
FIG. 21B illustrates a top view of the fixture from FIG. 21A shown here with the lid removed and tubing detached.
Figure 21C:
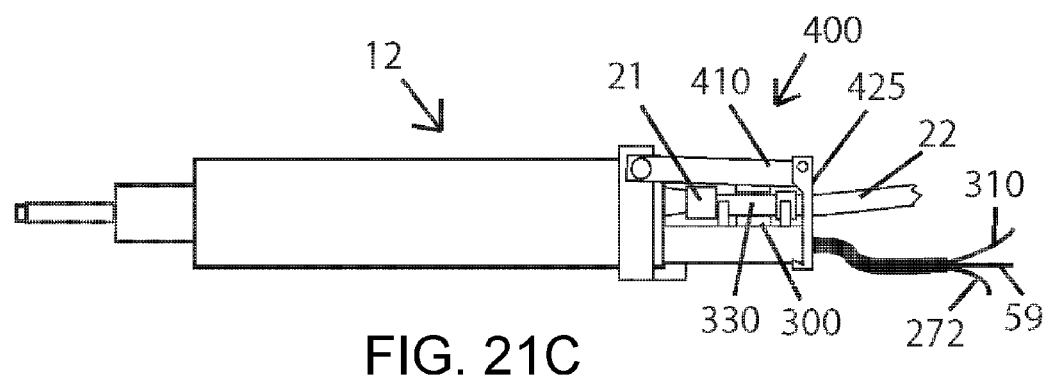
FIG. 21C illustrates a side view of the fixture from FIG. 21A shown here with the lid closed and tubing attached ready for operation.

Shown in FIGS. 21A, 21B and 21C is a sensor fixture 400 that can include sensor 300 in the form of load cell 320 (see FIGS. 8 and 9) about perpendicularly adjusted and slightly compressing the walls of a segment of elastic collapsible tubing 330 inserted near the distal end of aspiration path 23. Similarly to the fixture of FIG. 10, fixture 400 can have a hinged lid 410 incorporating a locking latch 425 and tubing guides 420. In this way tubing portions 278 (see FIG. 10) and 330 together with aspiration line 22 distal connector 21 can be detachably coupled to hand piece 12.

As in FIG. 10, fixture 400 can be a stand-alone unit or it can be integrated to a surgical hand piece 12. Collapsible tubing 330 is selected to preserve a patent fluid channel and remain in effective contact with load cell 320 across the full range of vacuum levels produced by aspiration pump 26. The minimum possible inner diameter of tubing 330 should preferably be above 1.5 mm to avoid clogging by solid particles. A silicone tubing segment of about 8 mm length having 3.2 mm ID and 4.8 mm OD has shown to be operative for practicing this invention. Fluctuations in pressure inside the lumen of tubing 330 typical of occlusion break produce an expansion of the walls of tubing segment 330 exerting a force over load cell 320 that is a function of vacuum at that location. Load cell 320 produces an electrical signal that is proportional to the force detected from tubing 330 walls. This signal is transmitted across cable 310 to control module 50 for processing. The advantages of this configuration are, again, as already described in connection with FIG. 10. In general terms, sensor 300 must be accurate to detect the timing of the occlusion-break event, but not necessarily strictly accurate to provide a proportional signal to vacuum inside aspiration line 22, as already described for FIG. 10, and so may employ a similar range of sensor types and functionalities.

Figure 23A:
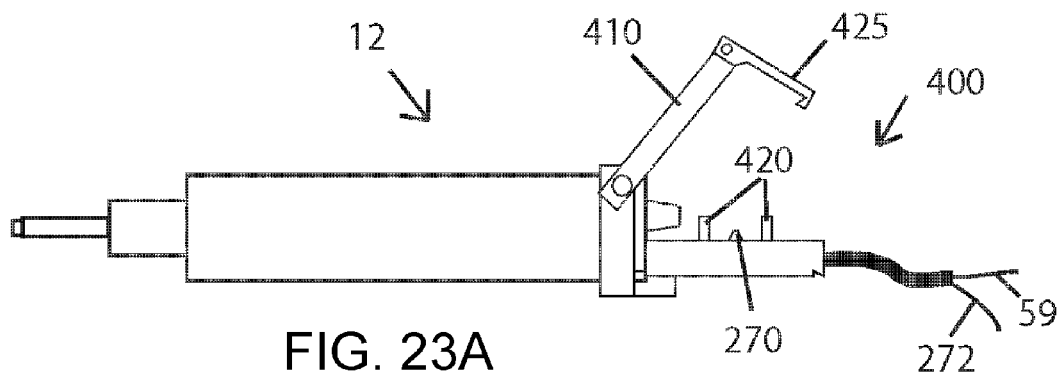
FIG. 23A illustrates a side view of a fixture that can hold an aspiration line blocking system of the present invention shown with the lid open and tubing detached.
Figure 23B:
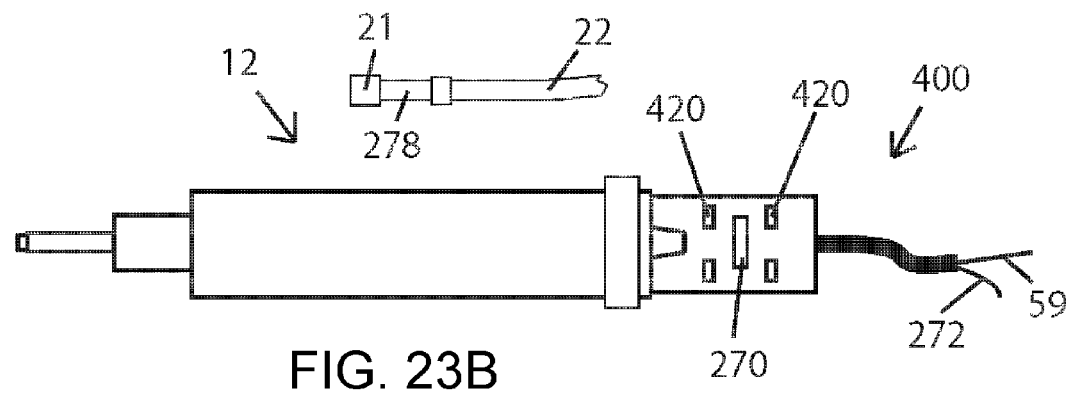
FIG. 23B illustrates a top view of the fixture from FIG. 23A shown here with the lid removed and tubing detached.
Figure 23C:
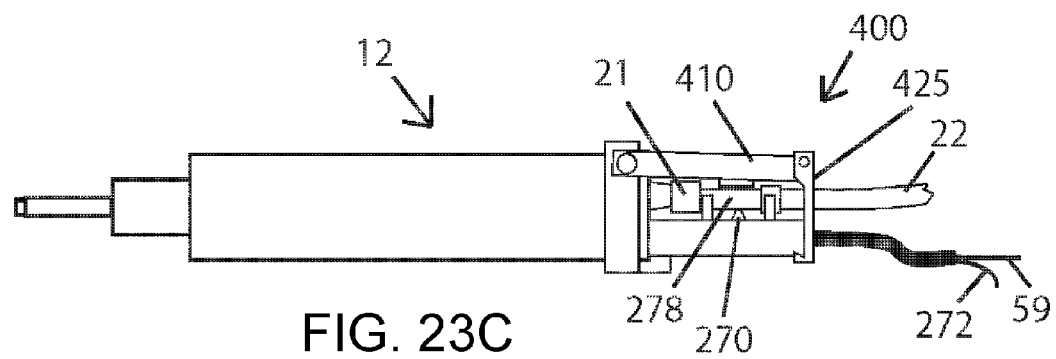
FIG. 23C illustrates a side view of the fixture from FIG. 23A shown here with the lid closed and tubing attached ready for operation.

Shown in FIGS. 23A, 23B and 23C is a valve fixture 400 that can have a hinged lid 410 incorporating a locking latch 425 and tubing guides 420. In this way tubing portion 278 together with aspiration line 22 distal connector 21 can be detachably coupled to hand piece 12. Fixture 400 can be a stand-alone unit or it can be integrated to a surgical hand piece 12. Collapsible tubing 278 is selected to preserve a patent fluid channel. The minimum possible inner diameter of tubing 330 (see FIG. 10) should preferably be above 1.5 mm to avoid clogging by solid particles. A silicone tubing segment of about 8 mm having 3.2 mm ID and 4.8 mm OD has shown to be operative for practicing this invention. This, again, is similar in most ways to what has already been discussed in relation to FIGS. 10 and 21.

Now, we examine the operation of these various embodiments of the invention in further detail.

During a typical lensectomy procedure, an operator introduces irrigation and aspiration probes 16 and 14 inside the eye through one small incision 94. Alternatively, irrigation and aspiration probes 16 and 14 can be introduced through separate incisions. The cataractous lens of the eye can be divided into fragments. The tip of lensectomy probe 14 is put in contact with the lens tissue and lens-disrupting power can be applied typically in the form of ultrasonic vibration of the probe tip while irrigation and vacuum are applied. Sometimes, the lens tissue can be removed by vacuum only. Setting console 11 foot pedal (input device) in positions 2 or 3 causes control module 50 to command having venting valve 57 closed, infusion valve 54 open and aspiration pump 26 operating up to a preset vacuum limit. With foot pedal in positions 2 or 3, when a lens fragment occludes the lensectomy probe tip, flow in the aspiration path 23 drops and vacuum can increase up to the maximum preset level.

In prior art systems, clearing of the probe tip from lens fragments thereby ending the occlusion allows fluid to escape the eye through aspiration path 23 at a rate faster than the rate at which irrigation probe 16 can replenish the eye, resulting in a chamber collapse caused by the post-occlusion surge, which presents a danger to the patient. With the present invention, when an occlusion-break event occurs at the tip of lensectomy probe 14, occlusion-break sensor 300 detects the onset and the magnitude of the vacuum change over time in aspiration path 23, and provides a vacuum signal to control console 50 to be converted into a dP/dt value. As a response to a dP/dt value reporting that an occlusion-break event has occurred, control module 50 can start a programmed occlusion-break control event. This response can comprise the following actions:

1) Commanding temporary closure of normally-open occlusion valve 270 by delivering at least one closing signal. Closure of normally-open occlusion valve 270 blocks the passage between hollow lensectomy probe 14 and aspiration line 22, stopping any fluid and particles from further escaping the eye through aspiration path 23. This action cancels the surge flowing out of the eye. Normally-open occlusion valve 270 can be fast operating, ideally with a response time below 30 milliseconds both for opening and closure for improved performance.

2) About simultaneously with closure of normally-open occlusion valve 270 (action 1), control module also commands the temporary opening of venting valve 57, allowing free flow of liquid between venting liquid deposit 58 and aspiration path 23. After closure of the fluid communication between the eye chamber and aspiration path 23 by normally-open occlusion valve 270 (action 1), aspiration path 23 proximal to valve 270 can retain an unrelieved negative pressure. Opening venting valve 57 (action 2) produces a rapid cancellation of this negative pressure by allowing a volume of fluid to displace by pressure gradient from venting liquid deposit 58 into aspiration line path 23. This flow terminates when the pressure difference across venting valve 57 equalizes. Venting valve 57 should be fast operating, ideally with a response time below 30 milliseconds both for opening and closure for improved performance. Operation of aspiration pump 26 can be modified by control module 50 for about the duration of normally-open occlusion valve 270 closure to expedite the vacuum cancellation effect of venting valve 57. This modification can comprise in a slow down, detent or even reverse operation. After ending of the occlusion and venting actions, the speed of pump 26 can be transitorily increased above normal for enhanced performance.

3) Control module 50 determines an optimal duration for the activation signals delivered to normally-open occlusion valve 270 and venting valve 57 (actions 1 and 2). These signals should be of the minimum effective duration in a way that chamber collapses are effectively cancelled while still allowing the system to resume normal operation rapidly. Control module can deliver fixed duration driving signals for valves 270 and 57. Alternatively, control module 50 can compute the duration of driving signals for valves 270 and 57 for improved performance, using for example the vacuum present at the onset of the occlusion break. As a mode of a non-limiting example, an algorithm that proved efficient to compute the duration of the driving signal for valves 270 and 57 in a particular setting was the following:

> IF dP/dt>+800 mmHg/sec THEN Pulse Duration=300+(Vacuum at break onset*0.8) milliseconds ELSE no blocking-venting action performed.

In a preferred modality, control module 50 can use a feedback loop to operate valves 270 and 57 until a determined level of vacuum relief in aspiration path 23 is achieved. The onset and duration of the driving signal for valves 270 and 57 can be synchronous or not. For computation of the optimal duration of these signals for effective pressure equalization, control module 50 can take into consideration factors such as lensectomy probe 14 resistance to flow, aspiration line 22 elastic properties, vacuum level at the onset of the occlusion break provided by aspiration line vacuum sensor 56 or sensor 300 (when available), rate of change of vacuum during the occlusion-break event (dP/dt), aspiration flow rate, irrigation pressure at eye level, resistance to flow of irrigation path including resistance of infusion probe 16, and wound size, among other factors. Experimental practice of the present invention using an Infiniti Console™, an Intrepid Cassette™, a 0.9 mm tapered Micro-Tip™ and an Ultra-Sleeve™ (all from Alcon Laboratories, USA.) has taught that when using actuator signals of similar duration for normally-open occlusion valve 270 closure and for venting valve 57 opening, the optimal duration of these pulses ranged between 30 milliseconds and 800 milliseconds depending on aspiration path 23 vacuum at the onset of the occlusion break. Duration of the driving signals for actuator 270 and venting valve 57 had to be increased with increasing occlusion break onset vacuum levels for proper chamber collapse control. Control module 50 can determine the optimal pulse duration for a given occlusion-break situation by using a pre-built look-up table stored in ROM. Alternatively a pre-built formula incorporating a set of the aforementioned parameters can be used. Also, a servo loop can be used to terminate the chamber collapse canceling actions 1 and 2 by monitoring the signals from aspiration line vacuum sensor 56 and/or from occlusion-break sensor 300 in real time. Once the signals coming from these sensors tell control module 50 that vacuum inside aspiration path 23 has reversed back from a potentially dangerous range to desirable, safe levels, actions 1 and 2 can be terminated. Initiation and termination of actions 1 and 2 can occur simultaneously or not, depending of the chamber collapse suppressing algorithm used by control module 50.

4) An optional action can comprise having control module 50 deliver an inhibit signal to hand piece power driver 52 in a way that the lens-disrupting power delivered by lensectomy probe 14 is reduced to safe levels during the programmed interval of occlusion and venting. In other words, the control system causes energy delivered to the tissue-disrupting probe 14 to be reduced or suspended as flow rates are reduced or suspended, to avoid risk of burn injury to body tissue being operated upon. This action may be of particular importance with ultrasonically-operated lensectomy probes 14 to avoid wound thermal injuries caused by lack of effective cooling during the programmed occlusion.

In an alternative embodiment, the vacuum relieving action 2 can instead be performed by slowed, stopped, or even reversed operation of aspiration pump 26. Speed and duration of this reverse operation may be controlled by control module 50 using a predetermined formula or a servo mechanism based on vacuum sensor 56 and/or detector 300 readings.

In another alternative embodiment, the vacuum relieving action 2 performed by venting valve 57 can be performed using pressurized fluid. Also normally closed venting valve 57 and normally open valve 270 can be replaced by a single two way pinch valve (1 N.O and 1 N.C) to simultaneously perform the actions of occlusion and venting of aspiration line 22. This two way valve modality can be installed at the distal portion of the aspiration path 23 for better performance.

When using irrigation line 18 as the source of the pressurized fluid, practice of this embodiment showed a reduced performance due to less fluid available to refill the eye chamber in the post-occlusion-break period. An embodiment shown in FIG. 18 circumvents this limitation by including a fluid source 900 containing a low impedance fluid buffer 910 for venting valve 57 while deriving fluid from irrigation line 18 across a fluidic resistance 920 composed by a narrow passage of 0.2 mm diameter. In this way a quick fluid removal from buffer 910 does not affect fluid availability for infusion into the eye through probe 16. In other words, fluid reservoir 910 accumulates fluid from said irrigation path 18 while the normally-closed venting valve 57 is closed, wherein, when normally-closed venting valve 57 is temporarily opened, the accumulated fluid in fluid reservoir 910 flows into aspiration path 23, to reduce the vacuum thereby preventing said vacuum surge and consequent body chamber collapse.

The liquid extracted by venting valve 57 activation is slowly replaced through resistance 920 when venting valve 57 is closed. FIG. 18 also illustrates an embodiment where all valves are disposed in a valve array 850 of one normally open valve 270 and two normally closed valves 57 and 572. All three valves can change state simultaneously driven by a single actuator (see, e.g., FIG. 14 for a two-valve example of this). In operation valve 270 allows vacuum from a high vacuum source 626 to aspirate fluid from hollow probe 14. In the event of an occlusion, vacuum source can build vacuum up to a preset limit that can be above 700 mmHg vacuum. Either by the action of vacuum alone, or by concurrent delivery of lens-disrupting power by hollow probe 14, occlusion at the tip probe 14 by lens fragments can break, allowing fluid to escape the eye towards aspiration path 23.

As a consequence of fluid entering aspiration path 23, a drop in vacuum will occur that will be detected by sensor 300. A rate of change of vacuum over time value is processed by controller 50 and can activate operation of all valves in valve array 850. The activation signal sent from controller 50 to valve array 850 produces a transitory closure of valve 270 blocking the surge into aspiration line 22. Simultaneously, venting valve 57 is open and provides a low-impedance source of vacuum canceling fluid into aspiration line 22. Also simultaneously, valve 572 opens providing an alternative aspiration path that maintains flow across probe 14 after occlusion break and during the surge cancellation cycle.

Low vacuum source 526 provides an adjustable vacuum level that is lower than the vacuum level provided by primary vacuum source 626. Vacuum limit available across alternative aspiration line 522 from vacuum source 526 is adjusted to a level capable of sustaining flow across probe 14 to maintain basic functionality and probe cooling capabilities during each surge canceling cycle. The embodiment of FIG. 18 accommodates all valves, sensor 300 and vacuum canceling fluid source in a single location preferably as near as possible to probe 14.

Figure 3:
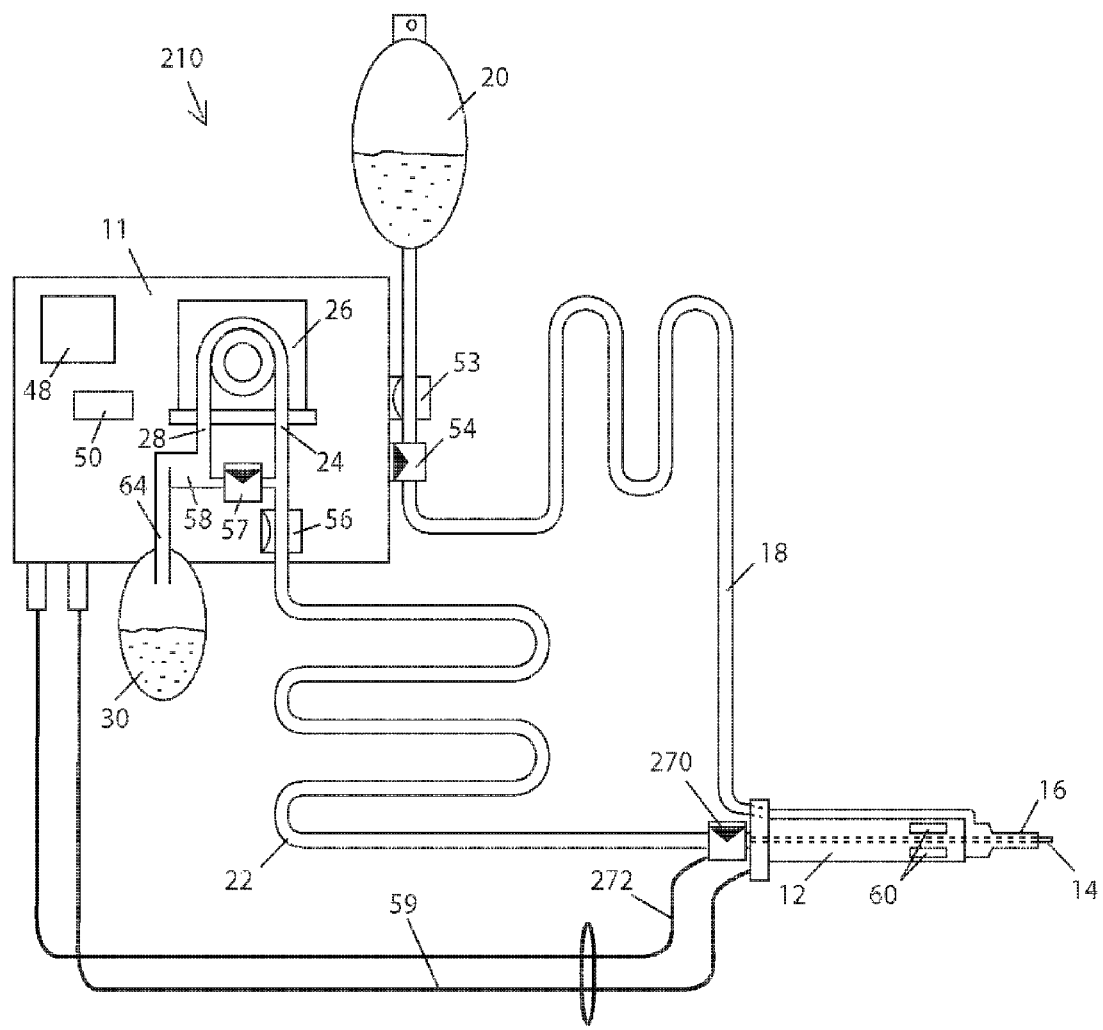
FIG. 3 is an illustration of another embodiment of the lensectomy system of the present invention.
Figure 5:
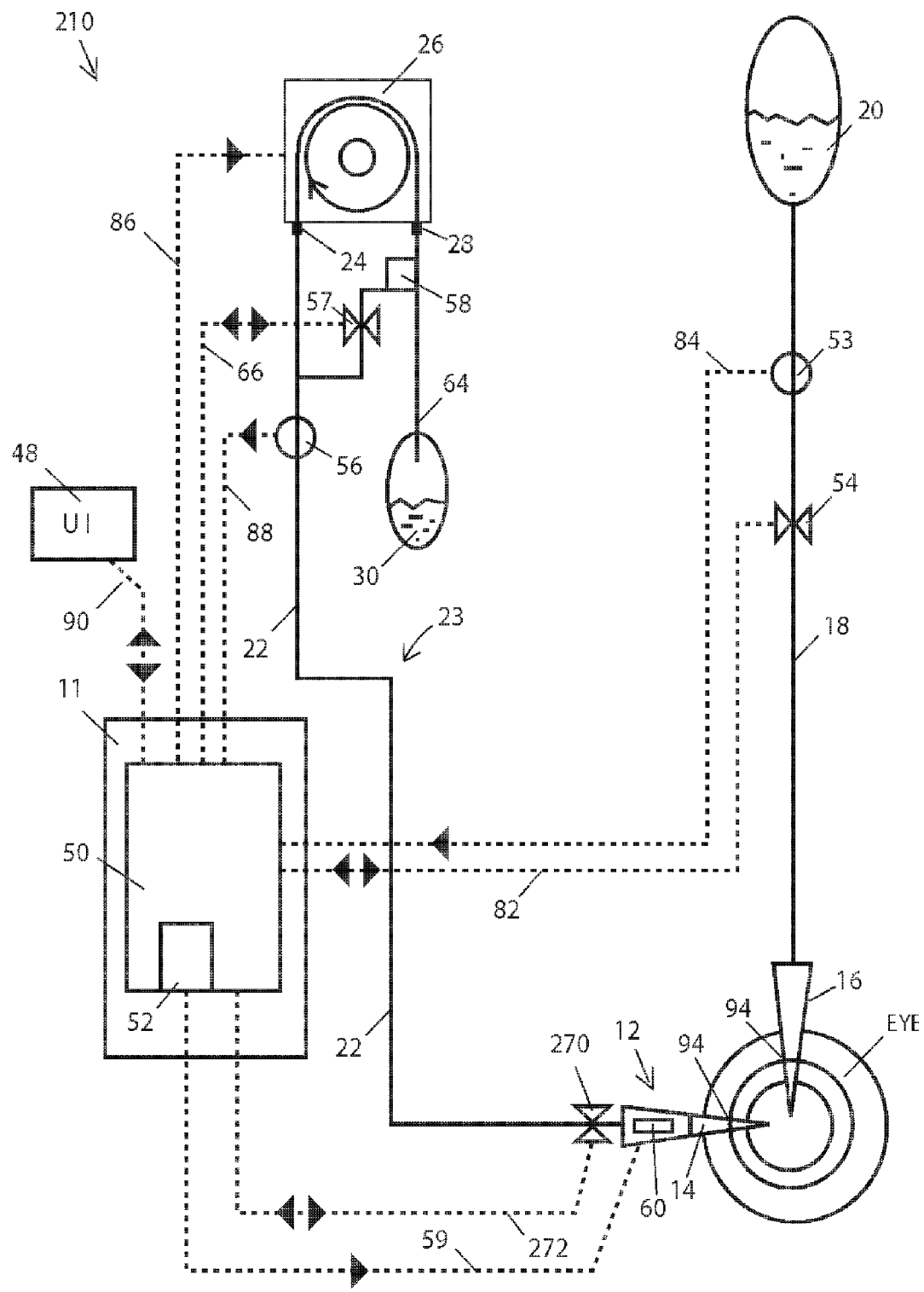
FIG. 5 is a schematic illustration of an alternative preferred embodiment of the present invention.
Figure 6A:
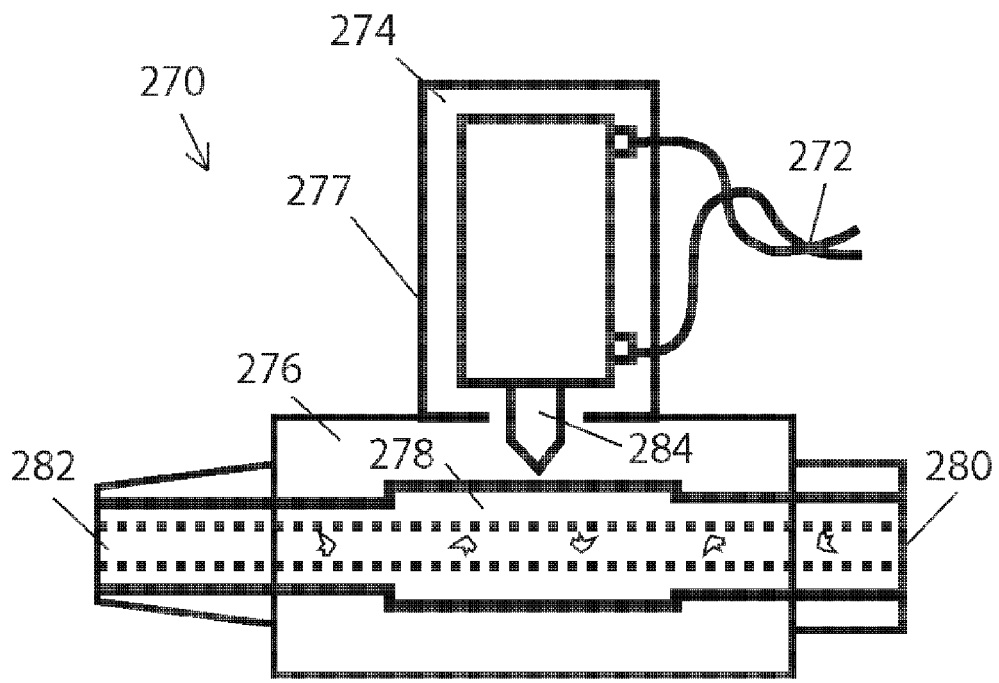
FIG. 6A is an illustration of one embodiment for an aspiration line blocking system corresponding to a pinch valve system shown in open condition.
Figure 6B:
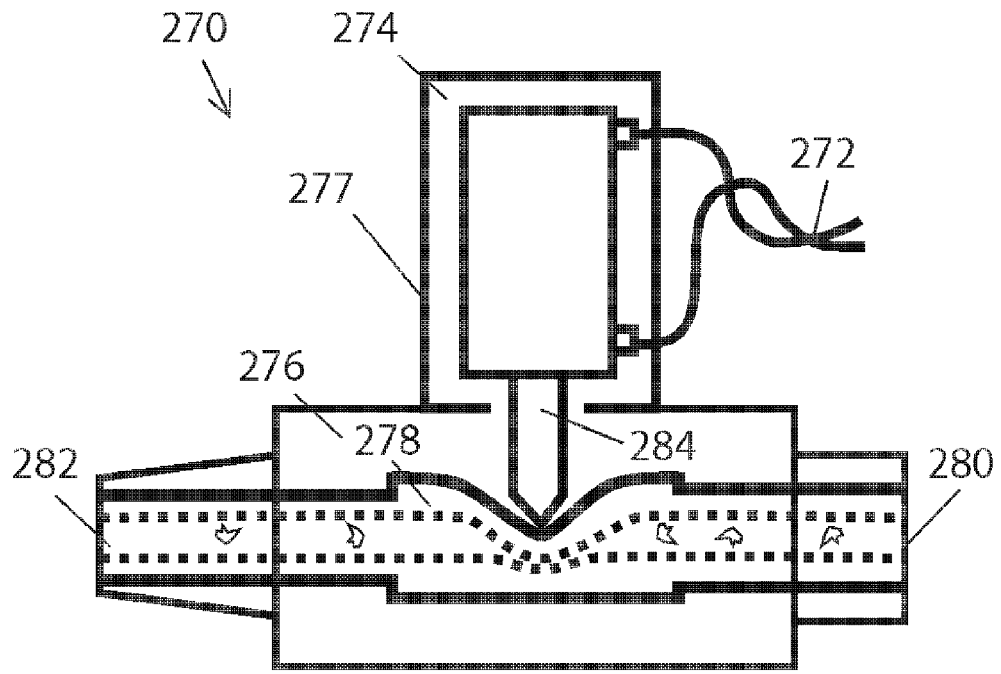
FIG. 6B is an illustration of the embodiment of FIG. 6A for an aspiration line blocking system shown in closed condition.

In an alternative embodiment depicted in FIG. 3 and FIG. 5, the function of occlusion-break sensor 300 located distally in aspiration path 23 is replaced by aspiration line vacuum sensor 56 typically located at console 11. A dP/dt value is derived from sensor 56 readings to trigger the post-occlusion surge response from control module 50. The duration of the occlusion and venting intervals can be fixed, computed or controlled by a feedback loop including a sensor 56 or 300. In a preferred embodiment, control module 50 uses a feedback loop.

FIG. 12 and FIG. 13 further incorporate an alternative aspiration path to a lower vacuum level that only enters into operation during each cycle of surge cancellation process of the present invention. This embodiment can be considered to avoid full inhibition of fluid circulation across probe 14 during each surge cancellation cycle. It can be considered advantageous particularly when practicing the present invention with ultrasonic disruption of the lens. In this situation, a transient full suppression of flow across probe 14 could promote wound thermal injuries by heat buildup caused by lack of cooling flow.

Some increase in performance can be noted by early restoration of flow into the eye across probe 16 and continued removal of fluid and particles across probe 14, without pausing during the surge canceling cycles. When an occlusion-break event is detected at control module 50 level by analysis of sensor 300 signal, typically a fast drop in aspiration path 23 vacuum level, a surge-canceling event can be triggered. In this embodiment, an activation signal is sent to transitorily close normally open valve 270. About simultaneously, an activation signal is sent to transitorily open normally closed venting valve 57. Additionally an activation signal is sent about simultaneously to transitorily activate normally closed valve 572. Valve 572 provides an alternative vacuum path for fluid flow aspirated though hollow probe 14 from the inside of the eye during the lapse that aspiration line 22 is fully blocked during the surge cancellation cycle.

Valve 572 opens a source of relatively low vacuum 526 typically in the range of 50 to 200 mmHg, across line 522 connected to vacuum source 526. Vacuum source 526 can adjust vacuum levels available at valve 572 across line 522 using a vacuum sensor 510. Peristaltic, Venturi and other pump mechanisms can be used as secondary low vacuum source 526. The alternative source of low vacuum sustains aspiration force across probe 14 improving cooling and particle removal during surge canceling cycles.

FIG. 14A and FIG. 14B shows an embodiment of a two-way pneumatic pinch valve that can be used in the implementation of the present invention, as an alternative to electromagnetic valves. The device can be designed as a single or a multiple way valve. The embodiment shown here can be used in the present invention to implement together normally open valve 270 and normally closed valve 572. FIG. 14A shows the valve in resting position. When activating a cycle of surge cancellation activity, a pulse of compressed gas is delivered into air chamber 718 though conductor 272 from a pressurized air source under controller 50 command.

Valve 700 normally open portion 728 is closed by the action of plunger 716 exerting pressure transmitted from air chamber 718 by displacement of diaphragm 720 attached to plunger 716 and compressing spring 724. Simultaneously, the blocking action exerted by plunger 716 transmitting spring 724 expansion force in the normally closed portion 710 of valve 700 is relieved opening the valve as shown in FIG. 14B. Once the pressure pulse delivered into chamber 718 ends, spring 724 re-expands displacing plunger 716 and diaphragm 720 back to the resting position blocking valve portion 710 and opening valve portion 728. Valve portion 710 of dual valve array 700 can replace discrete valve 270 while valve portion 728 can replace discrete valve 572.

Figure 19:
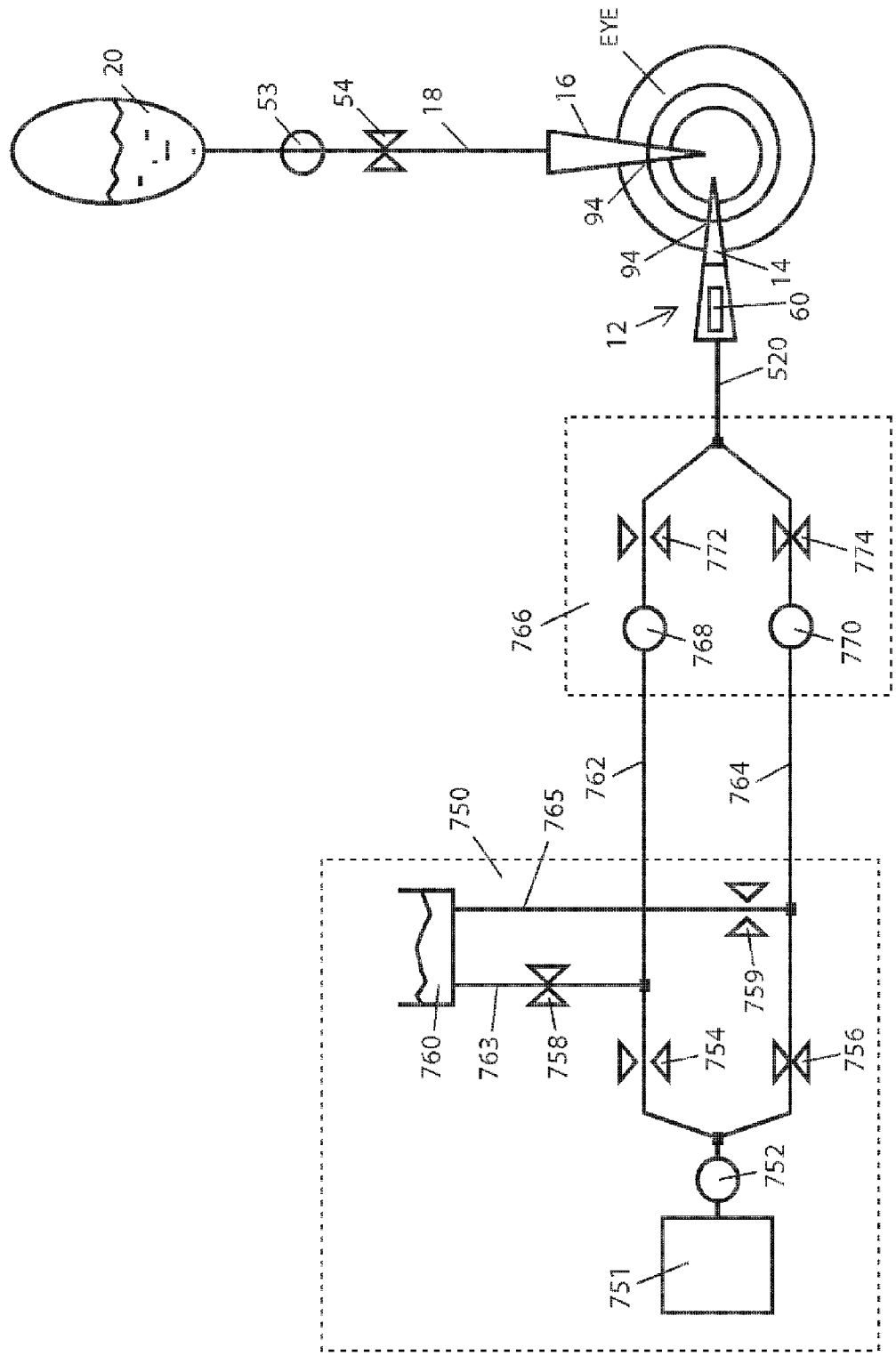
FIG. 19 is a schematic illustration of an embodiment using a dual aspiration path and a single aspiration pump.

Shown in FIG. 19 is an alternative embodiment of a blocking and venting surge cancelling system of the present invention using a single vacuum source, wherein aspiration path 23 is split into dual aspiration lines. A proximal system portion 750 is located near or at console 11. A vacuum source 751 has a proximal vacuum sensor 752 in line with a first and second aspiration line 762 and 764. Aspiration lines 762 and 764 join into a common aspiration line 520 in fluid communication with the aspiration channel of hollow lensectomy probe 14. Optional vacuum sensors 768 and 770 are installed in aspiration lines 762 and 764 respectively. First aspiration line 762 is connected to common line 520 having installed a proximal normally open valve 754 and a distal normally open valve 772. First aspiration line 762 also receives a venting line 763 having installed a normally closed valve 758. Second aspiration line 764 is connected to common line 520 having installed a proximal normally closed valve 756 and a distal normally open valve 774. Second aspiration line 764 also receives a venting line 765 having installed a normally open valve 759. Venting lines 763 and 765 can be connected to a fluid reservoir 760 or to a gas source such as air depending on the venting modality preferred for operation. The embodiment shown in FIG. 19 operates to first detect an occlusion-break event using sensors 768 and/or 752. After a threshold occlusion break is detected, controller 50 operates valves 754, 772 and 759 to transitorily close. About simultaneously, valves 756, 774 and 758 are operated to transitorily open. While valves 754 and 772 are closed, valve 758 is open, allowing venting of line 762. The actuation of valves 754, 772, 759 756, 774 and 758 is preferably ended when a vacuum is detected by sensors 752 or 768 to be at a desired level. While line 762 is being vented, aspiration is performed by line 764 having valves 756 and 774 open and valve 759 closed. This embodiment allows continuous aspiration through channel 520 using a single aspiration pump 751 by venting one aspiration line while aspirating with the other and vice-versa during the occlusion-break events.

Figure 20A:
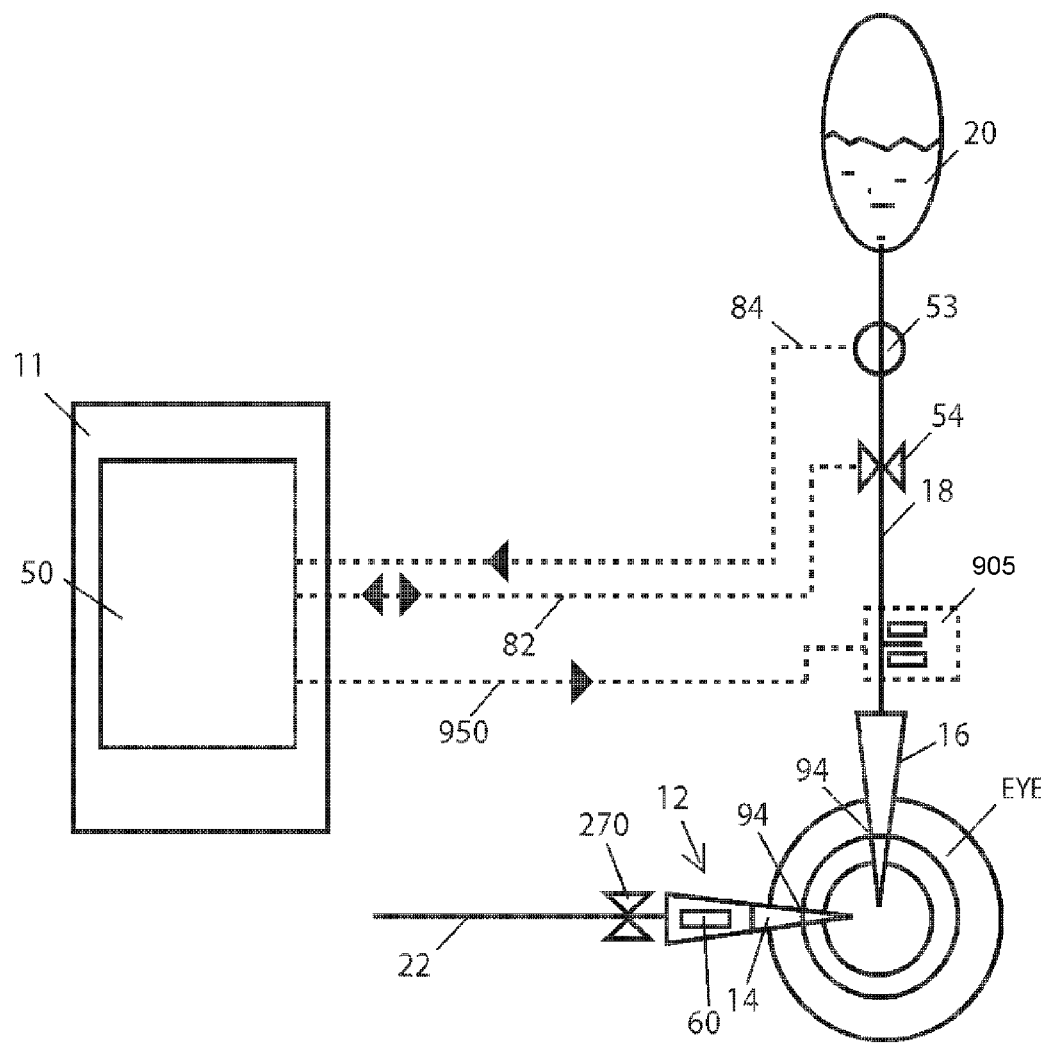
FIG. 20A and FIG. 20B illustrate a schematic view of an embodiment of the present invention incorporating an active irrigant injection system.

As regards the operation of the embodiment of FIG. 20A and FIG. 7B, controller 50 commands actuator 915 to act upon chamber 925 causing a contraction in synchronization with periods of enabled flow in aspiration path 23. In this way flow of irrigant solution into the eye chamber is boosted during periods of free flow. Activation of this irrigant injection system can cooperate to reduce eye chamber fluctuations caused by periods of enabled flow in the aspiration path. Actuator 915 can operate in proportional or fixed modes and the volume of irrigant solution to inject during each period can be adjusted under command of controller 50. Operation of active volume injector 905 is adjusted to compensate eventual chamber instabilities created by periods of free flow into aspiration line 22.

Figure 11:
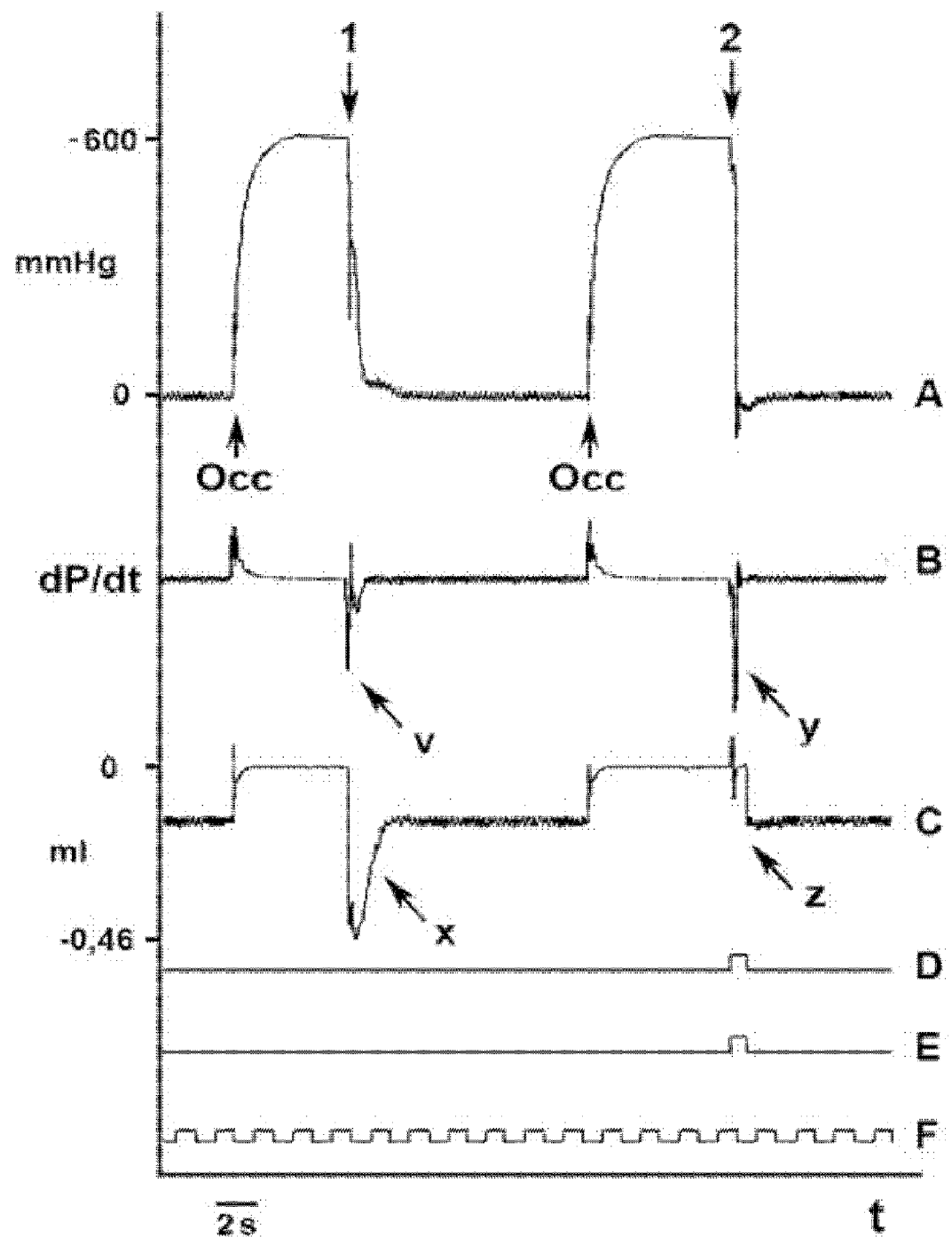
FIG. 11 is a chart recording depicting aspiration line vacuum, dP/dt and chamber collapse volume with (right) and without (left) the incorporation of the post-occlusion chamber collapse canceling system of the present invention.

FIG. 11 is a chart recording during experimental testing to demonstrate the advantage of practicing the present invention by comparing post-occlusion chamber collapse with and without operation of the system. This recording was made using an Infiniti console, a non-ABS tapered microtip, irrigant pressure set to 90 cm H2O and an Intrepid fluidics cassette (Alcon, USA). Tracing in A corresponds to aspiration line vacuum. B is the pressure differential, C is eye chamber volume, D is normally-open occlusion valve 270 activation signal, E is venting valve 57 activation signal. The left portion of the tracing depicts the relevant occlusion and post-occlusion events in a surgical system of the prior art. The arrow pointing up labeled Occ signals the start of an occlusion with vacuum rising up to 600 mmHg. Line F is a seconds mark, with each state transition spaced one second after the prior transition.

The arrow pointing down labeled 1 signals the moment of occlusion break. Aspiration line vacuum rapidly drops at a rate typically above 1500 mmHg/sec depicted in trace B (arrow v) translating into the chamber collapse seen in trace C (arrow x). Now turning to the right side of the chart recording, tracings from a surgical system incorporating the present invention are illustrated. The arrow pointing up labeled Occ signals the start of an occlusion event with vacuum rising to 600 mmHg in the aspiration line.

The arrow pointing down labeled 2 signals the moment of occlusion break. A peak of dP/dt shown in trace B (arrow y) is analyzed by control module 50 delivering an occlusion signal shown in D for normally-open occlusion valve 270 and a venting signal shown in E for venting valve 270. The computed value for the duration of these signals is 780 milliseconds. As can be observed in the right side of trace C (arrow z), there is virtually no evidence of chamber collapse as a consequence of occlusion break with the implementation of the present invention.

Figure 22:
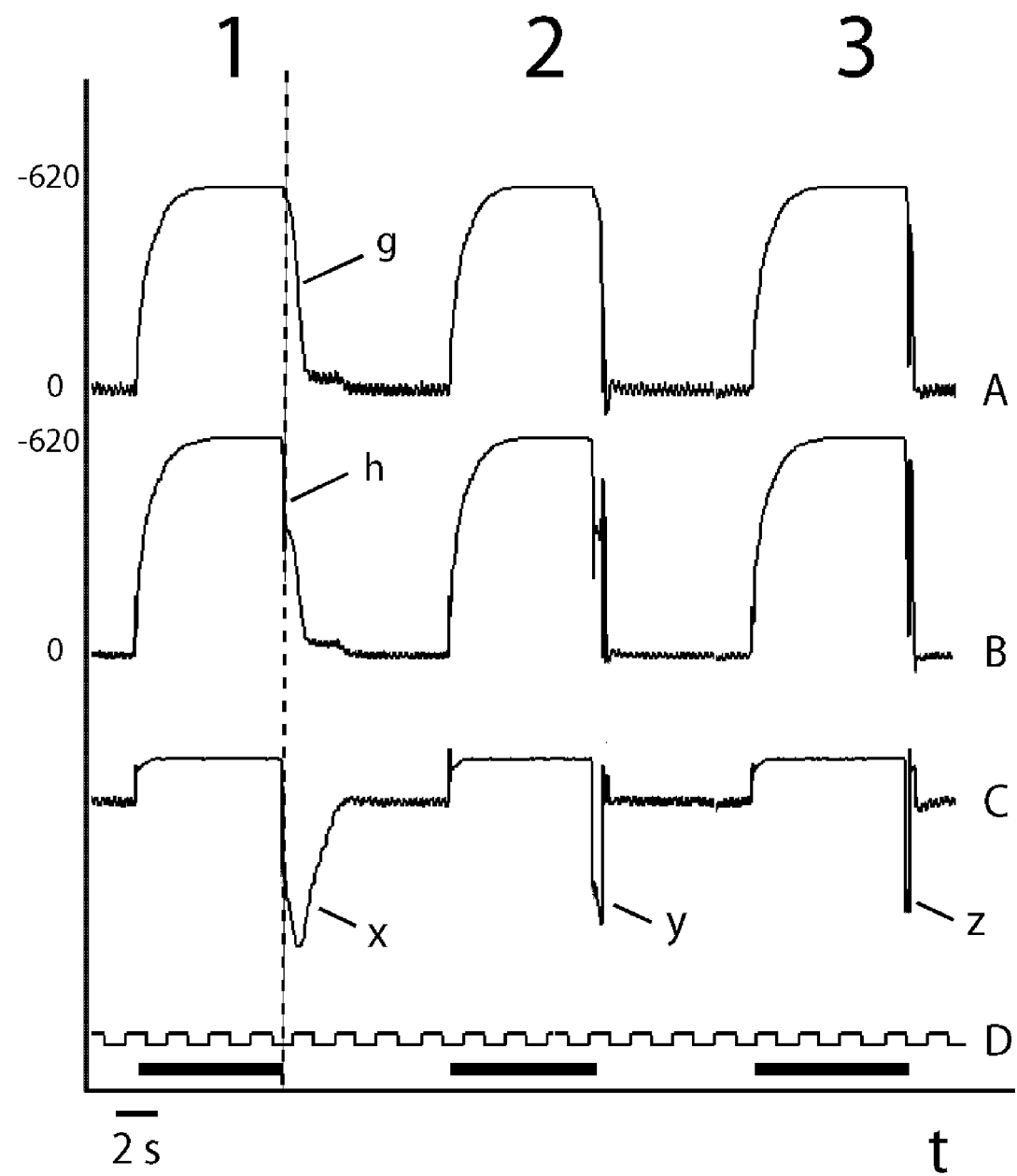
FIG. 22 is a chart recording depicting the chamber collapses observed with a standard surgical apparatus, in a surgical apparatus with a chamber collapse system of the prior art and in a surgical apparatus incorporating the chamber collapse canceling system of the present invention.

FIG. 22 is a chart recording that allows a comparison of the magnitude and duration of the chamber collapse in a standard system (1), a prior art system disclosed by Holden in U.S. 2006-0078448 (2), and with the present invention (3). Tracing A illustrates the vacuum readings from a sensor 300 located at the distal end of aspiration line 22, in vicinity to hand piece 12. Maximum vacuum readings are 620 mmHg. Tracing B illustrates simultaneous vacuum readings from a sensor 56 located at the proximal end of aspiration line 22 at console level. Tracing C depicts the chamber volume fluctuations. Tracing D is a time-mark with an interval of one second for each step. The 3 thick horizontal bars below the time-mark illustrate the periods of aspiration line occlusion. The negative spikes in C correspond to the chamber collapse events for embodiments 1, 2 and 3. Spike x has the biggest magnitude and duration and corresponds to a system without active cancellation of chamber collapse (1). Spike y has a reduced magnitude and duration when compared to (1) and corresponds to a system with an active cancellation system of the prior art (Holden). Spike z has a smallest magnitude and duration when compared to (1) and (2) and corresponds to a system with an active cancellation system of the present invention (3). A vertical dashed line is used to demonstrate the differences in timing to detect an occlusion-break event for a sensor located proximally (A) and distally (B) in aspiration line 22. Letters (g) and (h) show a latency of above 400 milliseconds for the peak dP/dt value.

Figure 24:
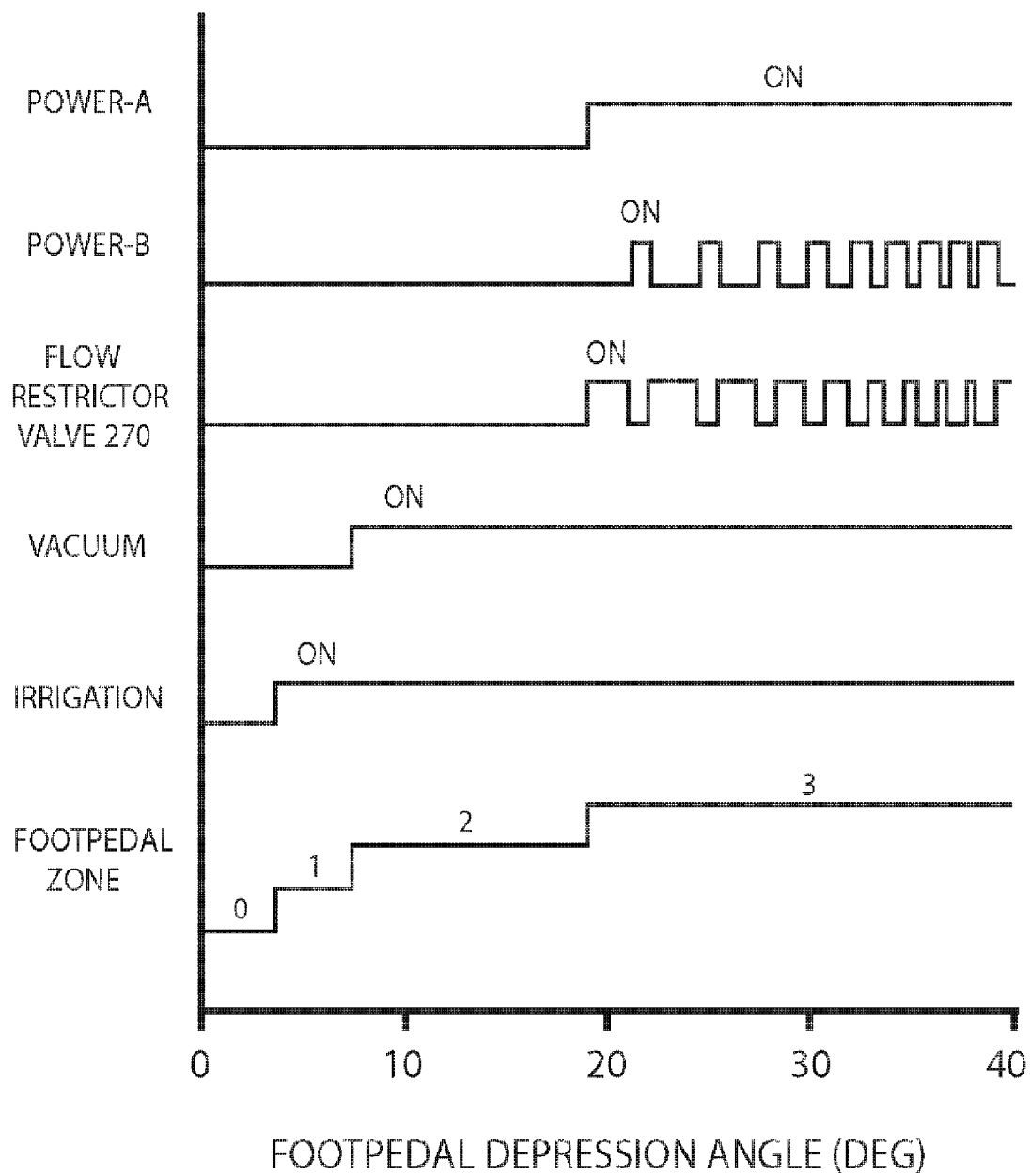
FIG. 24 is a graph depicting an example of a user commanded operation of a preferred embodiment of the flow control system of the present invention.

As shown in the example embodiment of FIG. 24, input device, e.g., footpedal 46 activation can determine that in zone 3 the system begins operating under command of control module 50. (While this discussion refers throughout to footpedal 46, it is understood that footpedal 46 is one non-limiting example of a user/operator interface and that any user interface with achieves a similar functional result is considered to be included within the scope of this disclosure and its associated claims.) On transitioning of footpedal 46 from zone 2 to zone 3, valve 270 can be activated to produce a continuous interruption of flow into aspiration line 22. As footpedal 46 is further depressed within zone 3, control module 50 can command valve 270 to start temporarily opening, allowing periods of free flow of known duration that can increment in frequency as footpedal 46 travels deeper across zone 3 reaching a maximum frequency at the end of footpedal travel in zone 3.

Figure 8:
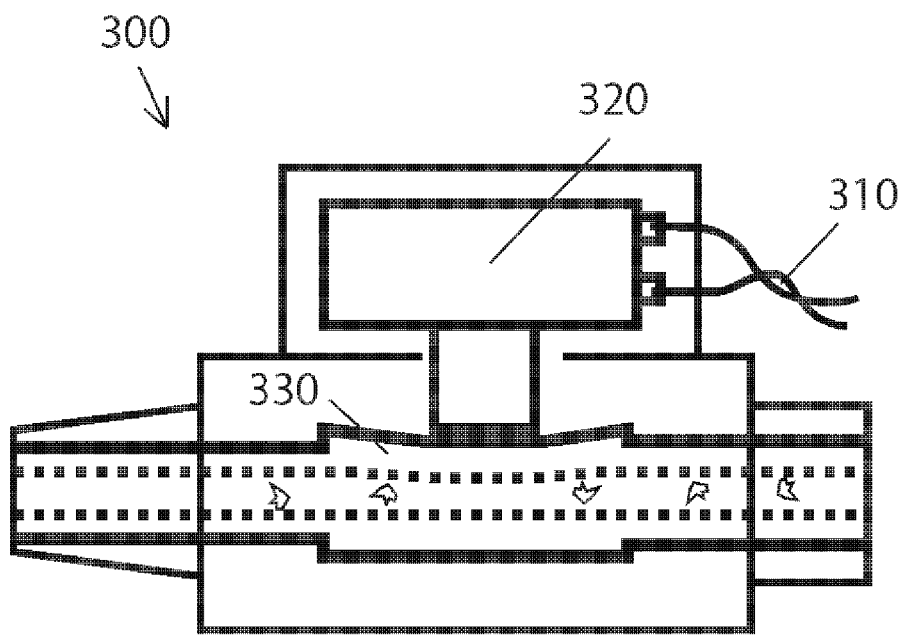
FIG. 8 is an illustration of one embodiment of an aspiration line occlusion-break sensing device operating by detecting force variations at the wall of tubing.
Figure 9:
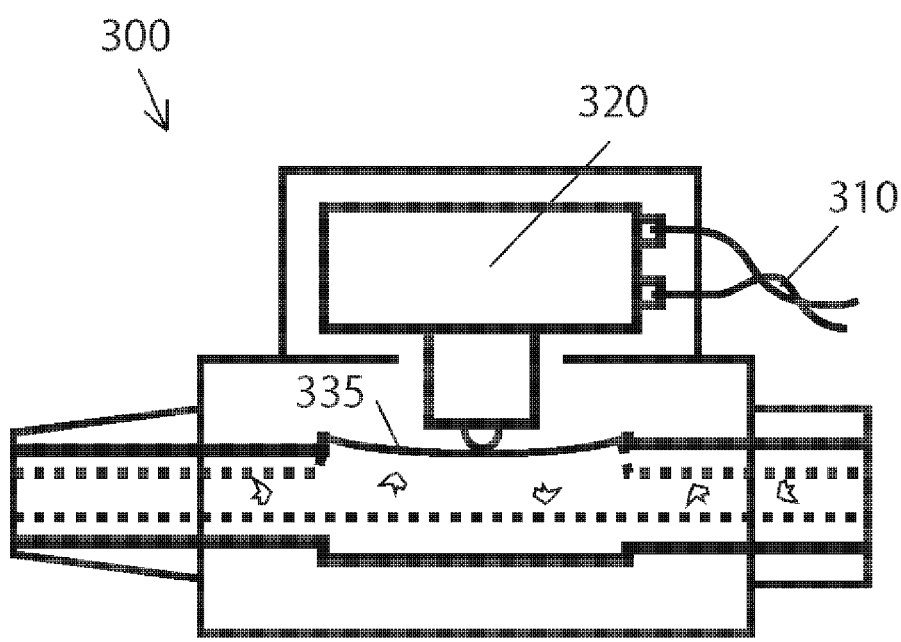
FIG. 9 is an illustration of another embodiment of an aspiration line occlusion-break sensing device that operates by detecting force variations in contact with a diaphragm.

Control module 50 can command simultaneous activation of lens-disrupting power during the free flow periods. Power applied to probe 14 can be independent of operation of valve 270 (FIG. 8, POWER-A), or can be synchronized with the activity of valve 270 by control module 50 (FIG. 8, POWER-B). When using a lens-disrupting power that can generate tissue damage under reduced flow conditions such as ultrasound, synchronization of power cycles to flow enabled periods is important for safe operation.

The duration of the periods of free flow into aspiration line 22 enabled by the opening of valve 270 can be constant within zone 3, or the duration can vary as footpedal 46 travels across zone 3. Vacuum level in aspiration line 22 can be the same in zones 2 and 3. Alternatively vacuum can vary under control module 50 command when footpedal 46 travels from zone 2 to zone 3, and also within zone 3.

Valve 270 can totally block flow into the aspiration line, or alternatively, it can reduce flow to a second, flow-restricted state which allows a reduced amount of flow into aspiration line 22. Shown in FIG. 7A is an optional valve bypass 299 to preserve some minimum flow across valve 270 when in closed condition. When the aspiration channel is totally blocked, any fragment entering the probe is no longer "pulled" by the probe tip and can be released away from the probe tip. A minimum of flow can prevent losing the grasp and facilitate to continue aspirating on the next cycle. This embodiment, therefore, allows an operator to safely grasp a tissue fragment with the tip of probe 14 while in the reduced flow condition (low flow), and remove this tissue fragment by then commanding a free flow period (high flow).

Depending on the type of valve selected for blocking valve 270, different implementations of valve bypass 270 can be incorporated. A notch or a perforation of known dimensions in a valve 270 lid and a bypass conduit of a selected diameter are two examples of such implementations. As a mode of example, a valve lid with a perforation with a diameter of 0.08 mm can be used when selecting to use a bypass to produce a flow of 8 milliliters per minute with valve 270 closed. A particles retaining filter 44, see, e.g., FIG. 7A, may be employed upstream of valve 270 to avoid bypass obstruction. Alternatively, a non-clogging valve such as a tissue-cutting chopper valve or a pinch valve can be used.

Valve 270 can be an ON-OFF valve or alternatively, it can be a proportional valve. When using a proportional valve, controller 50 can determine different waveforms for the timing of the opening and closing transitions of valve 270.

In a preferred embodiment of the present invention, control module 50 of console 11 is programmed to close flow restriction valve 270 when footpedal 46 travels from zone 2 to zone 3. As footpedal 46 is further depressed across zone 3, valve 270 is commanded to open for fixed periods lasting 30 milliseconds with an incremental repetition rate reaching a maximum of 12 periods per second at the end of travel of footpedal 46 within zone 3.

Maximum repetition rate of the free flow periods can be computed by control module 50 considering vacuum, pressure in irrigation line 18, resistance of infusion line 18 and resistance of aspiration line 22 to prevent clinically significant eye chamber fluctuations. Alternatively, duration and repetition rate of the free flow periods can be extracted by controller 50 from a lookup table stored in ROM or preset by an operator. In the second half of zone 3, lens-disrupting power can be incrementally added in synchronization with the periods of free flow.

Figure 20B:
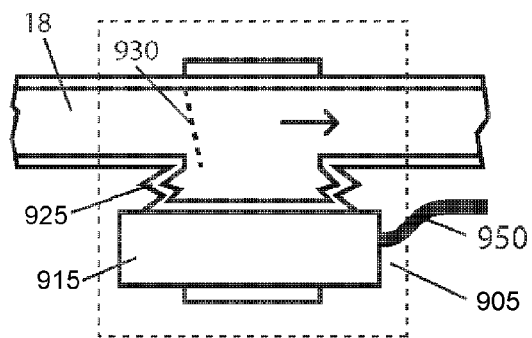

An alternative embodiment illustrated in FIG. 20A and FIG. 20B incorporates an active irrigant injection system installed in the distal portion of irrigation line 18. This injection system comprises an active volume injector 905 under command by controller 50 through injection system cable 950. Injector 905 is comprises a collapsible chamber 925 in fluid communication with irrigation line 18. Collapsible chamber 925 can be, for example not limitation, a bellows that can contract by the expansion of an collapse actuator 915. Actuator 915 can be an amplified piezoelectric actuator such as APA 400 from Cedrat, France. Many other actuators can be considered such as electromagnetic and ultrasonic. A check valve 930 can be installed upstream from collapsible chamber 925 to minimize irrigant reflow during operation.

In operation, controller 50 can command actuator 915 to act upon chamber 925 causing a contraction in synchronization with periods of enabled flow in aspiration path 23. In this way flow of irrigant solution into the eye chamber is boosted during periods of free flow. Activation of this irrigant injection system can cooperate to reduce eye chamber fluctuations caused by periods of enabled flow in the aspiration path. Actuator 915 can operate in proportional or fixed modes and the volume of irrigant solution to inject during each period can be adjusted under command of controller 50. Operation of active volume injector 905 is adjusted to compensate eventual chamber instabilities created by periods of free flow into aspiration line 22.

Thus, in conclusion, the reader will see that the post-occlusion chamber collapse canceling system of the present invention provides an effective and reliable improvement over the prior art allowing a surgeon to perform lensectomy procedures with high vacuum levels through smaller incisions. This feature leads to more efficient surgical procedures.

While the above description contains many specificities, these should not be construed as limitations on the scope of this invention but rather as an exemplification of the preferred embodiment thereof. In fact, the preferred embodiment has been fashioned to provide optimum performance at the reduced cost required for disposable surgical consumables. Many other variations are possible. For example venting valve 57 can be any kind of valve, electric, pneumatic or other. This valve can be an ON/OFF valve or a fast acting proportional valve and may be located in other position than console level.

Also, for example, aspiration line normally-open occlusion valve 270 can be any kind of ON/OFF valve or a fast acting proportional valve, such as a needle valve, acting in cooperation with a solid particles retaining filter to avoid clogging. Although valve 270 performs best when located at the distal end of aspiration path 23 near hollow probe 14, it can be located at other positions between probe 14 and pump 26, assuming a compromise in performance. A similar consideration can be made for occlusion-break sensor 300 regarding location.

Although this invention has been designed for use in ophthalmic surgery, other surgical procedures performed inside collapsible body chambers may benefit from its implementation. Accordingly, the scope of the invention should be determined not by the embodiments illustrated, but by the appended claims and their legal equivalents.

While only certain preferred features of the invention have been illustrated and described, many modifications, changes and substitutions will occur to those skilled in the art. It is, therefore, to be understood that the appended claims are intended to cover all such modifications and changes as fall within the true spirit of the invention.

I claim:

1. A surgical system for preventing collapse of a body chamber being operated upon, due to a vacuum surge following a clearing of an occlusion in an aspiration path (23) of said surgical system, comprising:
    an occlusion-break sensor (300) for sensing said clearing of said occlusion, wherein said occlusion-break sensor (300) is located proximate a distal end of said aspiration path (23), said aspiration path (23) further comprising a collapsible chamber (290) in fluidic connection therewith; wherein: following said clearing of said occlusion, said collapsible chamber (290) rapidly expands, thereby increasing the rate of pressure drop, and thereby increasing the sensitivity and response time of said occlusion-break detector sensor (300); and
    a normally-closed venting valve (57) temporarily opening in response to said occlusion-break sensor (300) sensing said clearing of said occlusion, to reduce the vacuum thereby preventing said vacuum surge and consequent body chamber collapse.

2. The system of claim 1, further comprising an irrigation path (18) thereof.

3. The system of claim 2, further comprising a bypass connection (960) between said irrigation path (18) and said aspiration path (23); said bypass connection (960) in turn comprising: said normally-closed venting valve (57), located proximate a distal end of said aspiration path (23); and a fluid reservoir (910) for accumulating fluid from said irrigation path (18) while said normally-closed venting valve (57) is closed; wherein: when said normally-closed venting valve (57) is temporarily opened, the accumulated fluid in said fluid reservoir (910) flows into said aspiration path (23), to reduce the vacuum thereby preventing said vacuum surge and consequent body chamber collapse.

4. The system of claim 1, wherein said body chamber is an eye.

5. The system of claim 1, further comprising a control system (50) returning said normally-closed venting valve (57) to a closed position in response to sensing that the danger of said vacuum surge has passed.

6. The system of claim 5, further comprising:
    a feedback vacuum sensor (56, 300); wherein: said returning said normally-closed venting valve (57) to a closed position is responsive to a signal of said feedback vacuum sensor (56, 300).

7. The system of claim 1, further comprising a control system (50) causing the temporary opening to last for a time that is computed using a formula.

8. The system of claim 1, further comprising a control system (50) causing the temporary opening to last for a time that is determined from a look up table.

9. The system of claim 1, wherein the temporary opening is caused to last less than 3000 milliseconds.

10. The system of claim 1, further comprising a control system (50) causing energy delivered to a tissue-disrupting probe (14) to be reduced or suspended during the temporary opening, to avoid risk of burn injury to body tissue being operated upon.

11. The system of claim 1, further comprising:
    an aspiration pump (26) within said aspiration path (23), capable of operating at a variety of flow rates in both forward and reverse directions including no flow in either direction; wherein: responsive to said occlusion-break sensor (300), said aspiration pump (26) is operated at said variety of flow rates, thereby preventing said vacuum surge and consequent body chamber collapse.

12. The system of claim 1, said occlusion-break sensor (300) comprising a sensor selected from the sensor group consisting of dP/dt sensors, vacuum sensors, pressure sensors, position sensors and flow sensors.

13. The system of claim 1, said normally-closed venting valve (57) comprising a valve selected from the valve group consisting of: a pinch valve, a tissue-cutting chopper valve, and a butterfly valve.

14. A surgical system for preventing collapse of a body chamber being operated upon, due to a vacuum surge following a clearing of an occlusion in an aspiration path (23) of said surgical system, said aspiration path (23) comprising a collapsible chamber (290) in fluidic connection therewith, comprising:
- an occlusion-break sensor (300) for sensing said clearing of said occlusion;
- a normally-open occlusion valve (270), temporarily closing in response to said occlusion-break sensor (300) sensing said clearing of said occlusion, thereby occluding fluid flow through said aspiration path (23) and controllably stabilizing said occlusion break, thereby preventing said vacuum surge and consequent body chamber collapse; and
- a normally-closed venting valve (57) temporarily opening in response to said occlusion-break sensor (300) sensing said clearing of said occlusion, to reduce the vacuum thereby preventing said vacuum surge and consequent body chamber collapse;
- wherein following said clearing of said occlusion, said collapsible chamber (290) rapidly expands, thereby increasing the rate of pressure drop, and thereby increasing the sensitivity and response time of said occlusion-break detector sensor (300).

15. The system of claim 14, wherein said occlusion-break sensor (300) is located proximate a distal end of said aspiration path (23).

16. The system of claim 14, wherein said normally-open occlusion valve (270) is located proximate a distal end of said aspiration path (23).

17. The system of claim 14, further comprising an irrigation path (18) thereof.

18. The system of claim 14, wherein said body chamber is an eye.

19. The system of claim 17, further comprising a bypass connection (960) between said irrigation path (18) and said aspiration path (23); said bypass connection (960) in turn comprising: said normally-closed venting valve (57), located proximate a distal end of said aspiration path (23); and a fluid reservoir (910) for accumulating fluid from said irrigation path (18) while said normally-closed venting valve (57) is closed; wherein: when said normally-closed venting valve (57) is temporarily opened, the accumulated fluid in said fluid reservoir (910) flows into said aspiration path (23), to reduce the vacuum thereby preventing said vacuum surge and consequent body chamber collapse.

20. The system of claim 19, further comprising a valve array (850), said valve array (850) comprising: said normally-closed venting valve (57) and said normally-open occlusion valve (270).

21. The system of claim 19, further comprising:
- a physical connection between said normally-closed venting valve (57) and said normally-open occlusion valve (270); wherein, as a consequence thereof: the opening of said normally-closed venting valve (57) and the closing of said normally-open occlusion valve (270) occurs substantially simultaneously; and the closing of said normally-closed venting valve (57) and the opening of said normally-open occlusion valve (270) occurs substantially simultaneously.

22. The system of claim 14, further comprising a control system (50) returning said normally-open occlusion valve (270) to an open position in response to sensing that the danger of said vacuum surge has passed.

23. The system of claim 22, further comprising: a feedback vacuum sensor (56, 300); wherein: said sensing that the danger of said vacuum surge has passed and returning said normally-open occlusion valve (270) to an open position is responsive to a signal of said feedback vacuum sensor (56, 300).

24. The system of claim 14, further comprising a control system (50) causing the temporary closing to last for a time that is computed using a formula.

25. The system of claim 14, further comprising a control system (50) causing the temporary closing to last for a time that is determined from a look up table.

26. The system of claim 14, wherein the temporary closing is caused to last less than 3000 milliseconds.

27. The system of claim 14, further comprising a control system (50) causing energy delivered to a tissue-disrupting probe (14) to be reduced or suspended during the temporary closing, to avoid risk of burn injury to body tissue being operated upon.

28. The system of claim 14, further comprising:
- an aspiration pump (26) within said aspiration path (23), capable of operating at a variety of flow rates in both forward and reverse directions including no flow in either direction; wherein: responsive to said occlusion-break sensor (300), said aspiration pump (26) is operated at said variety of flow rates, thereby preventing said vacuum surge and consequent body chamber collapse.

29. The system of claim 14, further comprising:
- a second normally closed-venting valve (572) located proximate said distal end of said aspiration path (23), temporarily opening in response to said occlusion-break sensor (300) sensing said clearing of said occlusion, to reduce the vacuum thereby preventing said vacuum surge and consequent body chamber collapse.

30. The system of claim 29, further comprising:
- a physical connection between said second normally-closed venting valve (572) and said normally-open occlusion valve (270); wherein, as a consequence thereof: the opening of said second normally-closed venting valve (572) and the closing of said normally-open occlusion valve (270) occurs substantially simultaneously; and the closing of said second normally-closed venting valve (572) and the opening of said normally-open occlusion valve (270) occurs substantially simultaneously.

31. The system of claim 14, said occlusion-break sensor (300) comprising a sensor selected from the sensor group consisting of dP/dt sensors, vacuum sensors, pressure sensors, position sensors and flow sensors.

32. The system of claim 14, said normally-open occlusion valve (270) comprising a valve selected from the valve group consisting of: a pinch valve, a tissue-cutting chopper valve, and a butterfly valve.

33. The system of claim 14, said normally-closed venting valve (57) comprising a valve selected from the valve group consisting of: a pinch valve, a tissue-cutting chopper valve, and a butterfly valve.

34. The system of claim 14, said normally-open occlusion valve (270) comprising a valve bypass (299) to preserve some flow across said normally-open occlusion valve (270) while said normally-open occlusion valve (270) is in a closed state, to preserve tissue fragment grasping and cooling capability.

35. The system of claim 14, further comprising:
a primary vacuum source (26, 626) for providing a primary vacuum for said aspiration path (23); a secondary vacuum source (526) for providing a secondary vacuum for said aspiration path (23); wherein: said secondary vacuum source (526) provides a reduced level of vacuum to preserve some flow across said aspiration path (23) while said normally-open occlusion valve (270) is in a closed state, to preserve tissue fragment grasping and cooling capability.

36. The system of claim 14, further comprising:
a split of said aspiration path (23) into a primary aspiration path (762) and a secondary aspiration path (764); said primary aspiration path (762) comprising at least said normally-open occlusion valve (270, 772, 774) and venting via said normally-closed venting valve (57, 758) associated therewith; and said secondary aspiration path (764) comprising at least one secondary normally-closed valve (756,770) and connected to a secondary normally-open valve (759) associated therewith;
wherein: actuation of the valves of and associated with said primary aspiration path (762) is oppositely-synchronized in relation to actuation of the valves of and associated with said secondary aspiration path (764), thereby enabling said primary aspiration path (762) to aspirate while said secondary aspiration path (764) is vented and enabling said primary aspiration path (762) to vent while said secondary aspiration path (764) is aspirated.

37. A surgical system for preventing collapse of a body chamber being operated upon, due to a vacuum surge following a clearing of an occlusion in an aspiration path (23) of said surgical system, comprising:
a normally-closed occlusion valve (270), temporarily opening for a defined interval before returning to a closed stated, and repeating said temporarily opening and closing at a controlled repetition rate, in response to control by an operator of said system, said normally-closed occlusion valve (270) comprising a valve bypass (299) to preserve some flow across said normally-closed occlusion valve (270) while said normally-closed occlusion valve (270) is in a closed state, to preserve tissue fragment grasping and cooling capability;
wherein: by opening said aspiration path (23) in response to said control by the operator, flow through said aspiration path (23) is controlled by the operator thereby preventing said vacuum surge and consequent body chamber collapse.

38. The system of claim 37, wherein said normally-closed occlusion valve (270) is located proximate said distal end of said aspiration path (23).

39. The system of claim 37, further comprising an irrigation path (18) thereof.

40. The system of claim 37, wherein said body chamber is an eye.

41. The system of claim 37, wherein said defined interval is determined by the operator.

42. The system of claim 37, wherein said defined interval is computed using a formula.

43. The system of claim 37, wherein said defined interval is determined from a look up table.

44. The system of claim 37, wherein said defined interval is less than 1000 milliseconds.

45. The system of claim 37, wherein said repetition rate is determined by the operator.

46. The system of claim 37, wherein said repetition rate is set to a predetermined value.

47. The system of claim 37, further comprising a control system (50) causing energy delivered to a tissue-disrupting probe (14) to be synchronized in relation to said opening and closing of said normally-closed occlusion valve (270), to avoid risk of burn injury to body tissue being operated upon.

48. The system of claim 47, wherein said energy delivered to said tissue-disrupting probe (14) is reduced or suspended whenever said normally-closed occlusion valve (270) is closed.

49. The system of claim 37, said normally-closed occlusion valve (270) comprising a valve selected from the valve group consisting of: a pinch valve, a tissue-cutting chopper valve, and a butterfly valve.

50. The system of claim 37, further comprising a particle retaining filter (44) to prevent said normally-closed occlusion valve (270) from clogging.

51. The system of claim 37, further comprising: a primary vacuum source (26, 626) for providing a primary vacuum for said aspiration path (23); a secondary vacuum source (526) for providing a secondary vacuum for said aspiration path (23); wherein: said secondary vacuum source (526) provides a reduced level of vacuum to preserve some flow across said aspiration path (23) while said normally-closed occlusion valve (270) is in a closed state, to preserve tissue fragment grasping and cooling capability.

52. A surgical system for preventing collapse of a body chamber being operated upon, due to a vacuum surge following a clearing of an occlusion in an aspiration path (23) of said surgical system, comprising:
an occlusion-break sensor (300) for sensing said clearing of said occlusion;
a normally-open occlusion valve (270), temporarily closing in response to said occlusion-break sensor (300) sensing said clearing of said occlusion, thereby occluding fluid flow through said aspiration path (23) and controllably stabilizing said occlusion break, thereby preventing said vacuum surge and consequent body chamber collapse; said normally-open occlusion valve (270) comprising a valve bypass (299) to preserve some flow across said normally-open occlusion valve (270) while said normally-open occlusion valve (270) is in a closed state, to preserve tissue fragment grasping and cooling capability; and
a normally-closed venting valve (57) temporarily opening in response to said occlusion-break sensor (300) sensing said clearing of said occlusion, to reduce the vacuum thereby preventing said vacuum surge and consequent body chamber collapse.

53. The system of claim 52, wherein said occlusion-break sensor (300) is located proximate a distal end of said aspiration path (23).

54. The system of claim 52, wherein said normally-open occlusion valve (270) is located proximate a distal end of said aspiration path (23).

55. The system of claim 52, further comprising an irrigation path (18) thereof.

56. The system of claim 52, further comprising a control system (50) returning said normally-open occlusion valve (270) to an open position in response to sensing that the danger of said vacuum surge has passed.

57. The system of claim 56, further comprising: a feedback vacuum sensor (56, 300); wherein: said sensing that the danger of said vacuum surge has passed and returning said normally-open occlusion valve (270) to an open position is responsive to a signal of said feedback vacuum sensor (56, 300).

58. The system of claim 52, further comprising a control system (50) causing the temporary closing to last for a time that is computed using a formula.

59. The system of claim 52, further comprising a control system (50) causing the temporary closing to last for a time that is determined from a look up table.

60. The system of claim 52, wherein the temporary closing is caused to last less than 3000 milliseconds.

61. The system of claim 52, further comprising a control system (50) causing energy delivered to a tissue-disrupting probe (14) to be reduced or suspended during the temporary closing, to avoid risk of burn injury to body tissue being operated upon.

62. The system of claim 52, further comprising:
an aspiration pump (26) within said aspiration path (23), capable of operating at a variety of flow rates in both forward and reverse directions including no flow in either direction; wherein: responsive to said occlusion-break sensor (300), said aspiration pump (26) is operated at said variety of flow rates, thereby preventing said vacuum surge and consequent body chamber collapse.

63. The system of claim 52, further comprising:
a second normally closed-venting valve (572) located proximate said distal end of said aspiration path (23), temporarily opening in response to said occlusion-break sensor (300) sensing said clearing of said occlusion, to reduce the vacuum thereby preventing said vacuum surge and consequent body chamber collapse.

64. The system of claim 63, further comprising:
a physical connection between said second normally-closed venting valve (572) and said normally-open occlusion valve (270); wherein, as a consequence thereof: the opening of said second normally-closed venting valve (572) and the closing of said normally-open occlusion valve (270) occurs substantially simultaneously; and the closing of said second normally-closed venting valve (572) and the opening of said normally-open occlusion valve (270) occurs substantially simultaneously.

65. The system of claim 52, said aspiration path (23) further comprising a collapsible chamber (290) in fluidic connection therewith; wherein: following said clearing of said occlusion, said collapsible chamber (290) rapidly expands, thereby increasing the rate of pressure drop, and thereby increasing the sensitivity and response time of said occlusion-break detector sensor (300).

66. The system of claim 55, further comprising a bypass connection (960) between said irrigation path (18) and said aspiration path (23); said bypass connection (960) in turn comprising: said normally-closed venting valve (57), located proximate a distal end of said aspiration path (23); and a fluid reservoir (910) for accumulating fluid from said irrigation path (18) while said normally-closed venting valve (57) is closed; wherein: when said normally-closed venting valve (57) is temporarily opened, the accumulated fluid in said fluid reservoir (910) flows into said aspiration path (23), to reduce the vacuum thereby preventing said vacuum surge and consequent body chamber collapse.

67. The system of claim 66, further comprising a valve array (850), said valve array (850) comprising: said normally-closed venting valve (57) and said normally-open occlusion valve (270).

68. The system of claim 66, further comprising:
a physical connection between said normally-closed venting valve (57) and said normally-open occlusion valve (270); wherein, as a consequence thereof: the opening of said normally-closed venting valve (57) and the closing of said normally-open occlusion valve (270) occurs substantially simultaneously; and the closing of said normally-closed venting valve (57) and the opening of said normally-open occlusion valve (270) occurs substantially simultaneously.

69. The system of claim 52, further comprising:
a primary vacuum source (26, 626) for providing a primary vacuum for said aspiration path (23); a secondary vacuum source (526) for providing a secondary vacuum for said aspiration path (23); wherein: said secondary vacuum source (526) provides a reduced level of vacuum to preserve some flow across said aspiration path (23) while said normally-open occlusion valve (270) is in a closed state, to preserve tissue fragment grasping and cooling capability.

70. The system of claim 52, further comprising:
a split of said aspiration path (23) into a primary aspiration path (762) and a secondary aspiration path (764); said primary aspiration path (762) comprising at least said normally-open occlusion valve (270, 772, 774) and venting via said normally-closed venting valve (57, 758) associated therewith; and said secondary aspiration path (764) comprising at least one secondary normally-closed valve (756,770) and connected to a secondary normally-open valve (759) associated therewith;
wherein: actuation of the valves of and associated with said primary aspiration path (762) is oppositely-synchronized in relation to actuation of the valves of and associated with said secondary aspiration path (764), thereby enabling said primary aspiration path (762) to aspirate while said secondary aspiration path (764) is vented and enabling said primary aspiration path (762) to vent while said secondary aspiration path (764) is aspirated.

71. A surgical system for preventing collapse of a body chamber being operated upon, due to a vacuum surge following a clearing of an occlusion in an aspiration path (23) of said surgical system, comprising:
an occlusion-break sensor (300) for sensing said clearing of said occlusion;
a normally-open occlusion valve (270), temporarily closing in response to said occlusion-break sensor (300) sensing said clearing of said occlusion, thereby occluding fluid flow through said aspiration path (23) and controllably stabilizing said occlusion break, thereby preventing said vacuum surge and consequent body chamber collapse;
a normally-closed venting valve (57) temporarily opening in response to said occlusion-break sensor (300) sensing said clearing of said occlusion, to reduce the vacuum thereby preventing said vacuum surge and consequent body chamber collapse; and
a split of said aspiration path (23) into a primary aspiration path (762) and a secondary aspiration path (764); said primary aspiration path (762) comprising at least said normally-open occlusion valve (270, 772, 774) and venting via said normally-closed venting valve (57, 758) associated therewith; and said secondary aspiration path (764) comprising at least one secondary normally-closed valve (756,770) and connected to a secondary normally-open valve (759) associated therewith;
wherein actuation of the valves of and associated with said primary aspiration path (762) is oppositely-synchronized in relation to actuation of the valves of and associated with said secondary aspiration path (764), thereby enabling said primary aspiration path (762) to aspirate while said secondary aspiration path (764) is vented and enabling said primary aspiration path (762) to vent while said secondary aspiration path (764) is aspirated.

72. The system of claim 71, wherein said occlusion-break sensor (300) is located proximate a distal end of said aspiration path (23).

73. The system of claim 71, wherein said normally-open occlusion valve (270) is located proximate a distal end of said aspiration path (23).

74. The system of claim 71, further comprising an irrigation path (18) thereof.

75. The system of claim 74, further comprising a bypass connection (960) between said irrigation path (18) and said aspiration path (23); said bypass connection (960) in turn comprising: said normally-closed venting valve (57), located proximate a distal end of said aspiration path (23); and a fluid reservoir (910) for accumulating fluid from said irrigation path (18) while said normally-closed venting valve (57) is closed; wherein: when said normally-closed venting valve (57) is temporarily opened, the accumulated fluid in said fluid reservoir (910) flows into said aspiration path (23), to reduce the vacuum thereby preventing said vacuum surge and consequent body chamber collapse.

76. The system of claim 75, further comprising a valve array (850), said valve array (850) comprising: said normally-closed venting valve (57) and said normally-open occlusion valve (270).

77. The system of claim 75, further comprising:
a physical connection between said normally-closed venting valve (57) and said normally-open occlusion valve (270); wherein, as a consequence thereof: the opening of said normally-closed venting valve (57) and the closing of said normally-open occlusion valve (270) occurs substantially simultaneously; and the closing of said normally-closed venting valve (57) and the opening of said normally-open occlusion valve (270) occurs substantially simultaneously.

78. The system of claim 71, further comprising a control system (50) returning said normally-open occlusion valve (270) to an open position in response to sensing that the danger of said vacuum surge has passed.

79. The system of claim 78, further comprising: a feedback vacuum sensor (56, 300); wherein: said sensing that the danger of said vacuum surge has passed and returning said normally-open occlusion valve (270) to an open position is responsive to a signal of said feedback vacuum sensor (56, 300).

80. The system of claim 71, further comprising a control system (50) causing the temporary closing to last for a time that is computed using a formula.

81. The system of claim 71, further comprising a control system (50) causing the temporary closing to last for a time that is determined from a look up table.

82. The system of claim 71, wherein the temporary closing is caused to last less than 3000 milliseconds.

83. The system of claim 71, further comprising a control system (50) causing energy delivered to a tissue-disrupting probe (14) to be reduced or suspended during the temporary closing, to avoid risk of burn injury to body tissue being operated upon.

84. The system of claim 71, further comprising:
an aspiration pump (26) within said aspiration path (23), capable of operating at a variety of flow rates in both forward and reverse directions including no flow in either direction; wherein: responsive to said occlusion-break sensor (300), said aspiration pump (26) is operated at said variety of flow rates, thereby preventing said vacuum surge and consequent body chamber collapse.

85. The system of claim 71, further comprising:
a second normally closed-venting valve (572) located proximate said distal end of said aspiration path (23), temporarily opening in response to said occlusion-break sensor (300) sensing said clearing of said occlusion, to reduce the vacuum thereby preventing said vacuum surge and consequent body chamber collapse.

86. The system of claim 85, further comprising:
a physical connection between said second normally-closed venting valve (572) and said normally-open occlusion valve (270); wherein, as a consequence thereof: the opening of said second normally-closed venting valve (572) and the closing of said normally-open occlusion valve (270) occurs substantially simultaneously; and the closing of said second normally-closed venting valve (572) and the opening of said normally-open occlusion valve (270) occurs substantially simultaneously.

87. The system of claim 71, said aspiration path (23) further comprising a collapsible chamber (290) in fluidic connection therewith; wherein: following said clearing of said occlusion, said collapsible chamber (290) rapidly expands, thereby increasing the rate of pressure drop, and thereby increasing the sensitivity and response time of said occlusion-break detector sensor (300).

88. The system of claim 71, said normally-open occlusion valve (270) comprising a valve bypass (299) to preserve some flow across said normally-open occlusion valve (270) while said normally-open occlusion valve (270) is in a closed state, to preserve tissue fragment grasping and cooling capability.

89. The system of claim 71, further comprising:
a primary vacuum source (26, 626) for providing a primary vacuum for said aspiration path (23); a secondary vacuum source (526) for providing a secondary vacuum for said aspiration path (23); wherein: said secondary vacuum source (526) provides a reduced level of vacuum to preserve some flow across said aspiration path (23) while said normally-open occlusion valve (270) is in a closed state, to preserve tissue fragment grasping and cooling capability.

90. A surgical system for preventing collapse of a body chamber being operated upon, due to a vacuum surge following a clearing of an occlusion in an aspiration path (23) of said surgical system, comprising:
an occlusion-break sensor (300) for sensing said clearing of said occlusion;
a normally-open occlusion valve (270), temporarily closing in response to said occlusion-break sensor (300) sensing said clearing of said occlusion, thereby occluding fluid flow through said aspiration path (23) and controllably stabilizing said occlusion break, thereby preventing said vacuum surge and consequent body chamber collapse;
a normally-closed venting valve (57) temporarily opening in response to said occlusion-break sensor (300) sensing said clearing of said occlusion, to reduce the vacuum thereby preventing said vacuum surge and consequent body chamber collapse;
a second normally closed-venting valve (572) located proximate said distal end of said aspiration path (23), temporarily opening in response to said occlusion-break sensor (300) sensing said clearing of said occlusion, to reduce the vacuum thereby preventing said vacuum surge and consequent body chamber collapse; and
a physical connection between said second normally-closed venting valve (572) and said normally-open occlusion valve (270); wherein the opening of said second normally-closed venting valve (572) and the closing of said normally-open occlusion valve (270) occurs substantially simultaneously; and the closing of said second normally-closed venting valve (572) and the opening of said normally-open occlusion valve (270) occurs substantially simultaneously.

91. The system of claim 90, wherein said occlusion-break sensor (300) is located proximate a distal end of said aspiration path (23).

92. The system of claim 90, wherein said normally-open occlusion valve (270) is located proximate a distal end of said aspiration path (23).

93. The system of claim 90, further comprising a control system (50) returning said normally-open occlusion valve (270) to an open position in response to sensing that the danger of said vacuum surge has passed.

94. The system of claim 90, further comprising a control system (50) causing energy delivered to a tissue-disrupting probe (14) to be reduced or suspended during the temporary closing, to avoid risk of burn injury to body tissue being operated upon.

95. The system of claim 90, further comprising:
an aspiration pump (26) within said aspiration path (23), capable of operating at a variety of flow rates in both forward and reverse directions including no flow in either direction; wherein: responsive to said occlusion-break sensor (300), said aspiration pump (26) is operated at said variety of flow rates, thereby preventing said vacuum surge and consequent body chamber collapse.

96. The system of claim 90, said aspiration path (23) further comprising a collapsible chamber (290) in fluidic connection therewith; wherein: following said clearing of said occlusion, said collapsible chamber (290) rapidly expands, thereby increasing the rate of pressure drop, and thereby increasing the sensitivity and response time of said occlusion-break detector sensor (300).

97. The system of claim 90, said normally-open occlusion valve (270) comprising a valve bypass (299) to preserve some flow across said normally-open occlusion valve (270) while said normally-open occlusion valve (270) is in a closed state, to preserve tissue fragment grasping and cooling capability.

98. The system of claim 90, further comprising:
a primary vacuum source (26, 626) for providing a primary vacuum for said aspiration path (23); a secondary vacuum source (526) for providing a secondary vacuum for said aspiration path (23); wherein: said secondary vacuum source (526) provides a reduced level of vacuum to preserve some flow across said aspiration path (23) while said normally-open occlusion valve (270) is in a closed state, to preserve tissue fragment grasping and cooling capability.

99. The system of claim 90, further comprising:
a split of said aspiration path (23) into a primary aspiration path (762) and a secondary aspiration path (764); said primary aspiration path (762) comprising at least said normally-open occlusion valve (270, 772, 774) and venting via said normally-closed venting valve (57, 758) associated therewith; and said secondary aspiration path (764) comprising at least one secondary normally-closed valve (756,770) and connected to a secondary normally-open valve (759) associated therewith;
wherein: actuation of the valves of and associated with said primary aspiration path (762) is oppositely-synchronized in relation to actuation of the valves of and associated with said secondary aspiration path (764), thereby enabling said primary aspiration path (762) to aspirate while said secondary aspiration path (764) is vented and enabling said primary aspiration path (762) to vent while said secondary aspiration path (764) is aspirated.

100. A surgical system for preventing collapse of a body chamber being operated upon, due to a vacuum surge following a clearing of an occlusion in an aspiration path (23) of said surgical system, comprising:
an occlusion-break sensor (300) for sensing said clearing of said occlusion;
a normally-open occlusion valve (270), temporarily closing in response to said occlusion-break sensor (300) sensing said clearing of said occlusion, thereby occluding fluid flow through said aspiration path (23) and controllably stabilizing said occlusion break, thereby preventing said vacuum surge and consequent body chamber collapse; and
a normally-closed venting valve (57) temporarily opening in response to said occlusion-break sensor (300) sensing said clearing of said occlusion, to reduce the vacuum thereby preventing said vacuum surge and consequent body chamber collapse;
an irrigation path (18);
a bypass connection (960) between said irrigation path (18) and said aspiration path (23); said bypass connection (960) in turn comprising: said normally-closed venting valve (57), located proximate a distal end of said aspiration path (23); and a fluid reservoir (910) for accumulating fluid from said irrigation path (18) while said normally-closed venting valve (57) is closed; wherein: when said normally-closed venting valve (57) is temporarily opened, the accumulated fluid in said fluid reservoir (910) flows into said aspiration path (23), to reduce the vacuum thereby preventing said vacuum surge and consequent body chamber collapse; and
a physical connection between said normally-closed venting valve (57) and said normally-open occlusion valve (270); wherein, as a consequence thereof: the opening of said normally-closed venting valve (57) and the closing of said normally-open occlusion valve (270) occurs substantially simultaneously; and the closing of said normally-closed venting valve (57) and the opening of said normally-open occlusion valve (270) occurs substantially simultaneously.

101. The system of claim 100, wherein said occlusion-break sensor (300) is located proximate a distal end of said aspiration path (23).

102. The system of claim 100, wherein said normally-open occlusion valve (270) is located proximate said distal end of said aspiration path (23).

103. The system of claim 100, further comprising a control system (50) returning said normally-open occlusion valve (270) to an open position in response to sensing that the danger of said vacuum surge has passed.

104. The system of claim 103, further comprising: a feedback vacuum sensor (56, 300); wherein said sensing that the danger of said vacuum surge has passed and returning said normally-open occlusion valve (270) to an open position is responsive to a signal of said feedback vacuum sensor (56, 300).

105. The system of claim 100, further comprising a control system (50) causing the temporary closing to last for a time that is computed using a formula.

106. The system of claim 100, further comprising a control system (50) causing the temporary closing to last for a time that is determined from a look up table.

107. The system of claim 100, wherein the temporary closing is caused to last less than 3000 milliseconds.

108. The system of claim 100, further comprising a control system (50) causing energy delivered to a tissue-disrupting probe (14) to be reduced or suspended during the temporary closing, to avoid risk of burn injury to body tissue being operated upon.

109. The system of claim 100, further comprising:
an aspiration pump (26) within said aspiration path (23), capable of operating at a variety of flow rates in both forward and reverse directions including no flow in either direction; wherein: responsive to said occlusion-break sensor (300), said aspiration pump (26) is operated at said variety of flow rates, thereby preventing said vacuum surge and consequent body chamber collapse.

110. The system of claim 100, further comprising:
a second normally closed-venting valve (572) located proximate said distal end of said aspiration path (23), temporarily opening in response to said occlusion-break sensor (300) sensing said clearing of said occlusion, to reduce the vacuum thereby preventing said vacuum surge and consequent body chamber collapse.

111. The system of claim 110, further comprising:
a physical connection between said second normally-closed venting valve (572) and said normally-open occlusion valve (270); wherein, as a consequence thereof: the opening of said second normally-closed venting valve (572) and the closing of said normally-open occlusion valve (270) occurs substantially simultaneously; and the closing of said second normally-closed venting valve (572) and the opening of said normally-open occlusion valve (270) occurs substantially simultaneously.

112. The system of claim 100, said aspiration path (23) further comprising a collapsible chamber (290) in fluidic connection therewith; wherein: following said clearing of said occlusion, said collapsible chamber (290) rapidly expands, thereby increasing the rate of pressure drop, and thereby increasing the sensitivity and response time of said occlusion-break detector sensor (300).

113. The system of claim 100, said normally-open occlusion valve (270) comprising a valve bypass (299) to preserve some flow across said normally-open occlusion valve (270) while said normally-open occlusion valve (270) is in a closed state, to preserve tissue fragment grasping and cooling capability.

114. The system of claim 100, further comprising:
a primary vacuum source (26, 626) for providing a primary vacuum for said aspiration path (23); a secondary vacuum source (526) for providing a secondary vacuum for said aspiration path (23); wherein: said secondary vacuum source (526) provides a reduced level of vacuum to preserve some flow across said aspiration path (23) while said normally-open occlusion valve (270) is in a closed state, to preserve tissue fragment grasping and cooling capability.

115. The system of claim 100, further comprising:
a split of said aspiration path (23) into a primary aspiration path (762) and a secondary aspiration path (764); said primary aspiration path (762) comprising at least said normally-open occlusion valve (270, 772, 774) and venting via said normally-closed venting valve (57, 758) associated therewith; and said secondary aspiration path (764) comprising at least one secondary normally-closed valve (756,770) and connected to a secondary normally-open valve (759) associated therewith;
wherein: actuation of the valves of and associated with said primary aspiration path (762) is oppositely-synchronized in relation to actuation of the valves of and associated with said secondary aspiration path (764), thereby enabling said primary aspiration path (762) to aspirate while said secondary aspiration path (764) is vented and enabling said primary aspiration path (762) to vent while said secondary aspiration path (764) is aspirated.

\* \* \* \* \*